United States Patent
Steger et al.

(10) Patent No.: US 11,564,760 B2
(45) Date of Patent: Jan. 31, 2023

(54) COMPUTER-ASSISTED TELEOPERATED SURGERY SYSTEMS AND METHODS

(71) Applicant: Intuitive Surgical Operations, Inc., Sunnyvale, CA (US)

(72) Inventors: John Ryan Steger, Sunnyvale, CA (US); Ryan Charles Abbott, San Jose, CA (US); Daniel H. Gomez, Los Gatos, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 954 days.

(21) Appl. No.: 16/340,966

(22) PCT Filed: Oct. 17, 2017

(86) PCT No.: PCT/US2017/056990
§ 371 (c)(1),
(2) Date: Apr. 10, 2019

(87) PCT Pub. No.: WO2018/075527
PCT Pub. Date: Apr. 26, 2018

(65) Prior Publication Data
US 2019/0231461 A1    Aug. 1, 2019

Related U.S. Application Data

(60) Provisional application No. 62/409,625, filed on Oct. 18, 2016.

(51) Int. Cl.
*A61B 90/50* (2016.01)
*A61B 34/35* (2016.01)
(Continued)

(52) U.S. Cl.
CPC .............. *A61B 34/35* (2016.02); *A61B 34/30* (2016.02); *A61B 50/20* (2016.02); *A61B 90/50* (2016.02);
(Continued)

(58) Field of Classification Search
CPC ........... Y10T 403/32; Y10T 403/32008; Y10T 403/32041; Y10T 403/32049; B25J 9/106;
(Continued)

(56) References Cited

U.S. PATENT DOCUMENTS 4,804,220 A * 2/1989 Rosheim .............. B25J 15/0009
                                                   403/114
5,279,309 A * 1/1994 Taylor .................... A61B 34/76
                                                    600/595
(Continued)

FOREIGN PATENT DOCUMENTS

CN          1642696 A       7/2005
CN        104546147 A       4/2015
(Continued)

OTHER PUBLICATIONS

Choi H., et al., "Surgical Robot for Single-Incision Laparoscopic Surgery," IEEE Transactions on Biomedical Engineering, Sep. 2014, vol. 61 (9), pp. 2458-2466.
(Continued)

*Primary Examiner* — Jennifer E. Novosad
(74) *Attorney, Agent, or Firm* — Fish & Richardson P.C.

(57) ABSTRACT

A computer-assisted teleoperated surgical system includes one or more manipulator devices and other components. A manipulator device includes a first link, a second link coupled to a distal end of the first link, a third link coupled to the second link, and an instrument actuator coupled to the third link. A joint that couples the second link to the first link defines a yaw axis. A joint that couples the third link to the
(Continued)

second link defines a pitch axis. The instrument actuator defines an insertion axis. The yaw, pitch, and insertion axes are fixed in relation to each other and intersect at a remote center of motion. The instrument actuator may insert a surgical instrument along the insertion axis roll and may roll the surgical instrument around the insertion axis. The proximal end of the first link may be coupled to a repositionable setup structure, which may optionally be mechanically grounded to an operating room table. A user control unit includes a processor that acts as a controller, and user inputs at the user control unit teleoperated the manipulator device via the controller.

20 Claims, 16 Drawing Sheets

(51) Int. Cl.
    *A61B 34/30*     (2016.01)
    *A61B 50/20*     (2016.01)
    *B25J 9/10*     (2006.01)
    *B25J 9/16*     (2006.01)
    *A61B 17/00*     (2006.01)
    *A61B 17/34*     (2006.01)

(52) U.S. Cl.
CPC ............ *B25J 9/106* (2013.01); *B25J 9/1689* (2013.01); *A61B 17/3423* (2013.01); *A61B 2017/00464* (2013.01); *A61B 2017/00477* (2013.01); *A61B 2034/301* (2016.02); *A61B 2034/305* (2016.02)

(58) Field of Classification Search
CPC ........ B25J 9/1689; A61B 50/20; A61B 90/50; A61B 34/35; A61B 34/30; A61B 2034/301; A61B 2034/305; A61B 17/3423; A61B 34/00; A61B 2017/00464; A61B 2017/00477; A61B 17/062; A61B 17/00; A61B 19/00; F16H 25/20
USPC ........................ 403/52, 53, 57, 58; 606/130
See application file for complete search history.

(56) References Cited

U.S. PATENT DOCUMENTS

| | | | | |
|---|---|---|---|---|
| 5,397,323 A * | 3/1995 | Taylor | ................... | A61B 34/71 901/41 |
| 5,792,135 A * | 8/1998 | Madhani | ................ | A61B 34/77 606/1 |
| 6,451,027 B1 * | 9/2002 | Cooper | .............. | A61B 1/00149 901/19 |
| 6,554,844 B2 * | 4/2003 | Lee | ...................... | A61B 5/0084 606/1 |
| 6,786,896 B1 * | 9/2004 | Madhani | ................ | A61B 34/30 606/1 |
| 6,902,560 B1 * | 6/2005 | Morley | .................. | A61B 34/30 606/1 |
| 8,004,229 B2 * | 8/2011 | Nowlin | .................. | A61B 34/77 318/568.2 |
| 8,151,661 B2 * | 4/2012 | Schena | .................. | A61B 34/37 242/157.1 |
| 8,444,631 B2 | 5/2013 | Yeung et al. | | |
| 9,173,643 B2 | 11/2015 | Morley et al. | | |
| 9,333,041 B2 * | 5/2016 | Yeung | ................... | A61B 34/30 |
| 11,135,027 B2 * | 10/2021 | Abbott | ................... | A61B 34/00 |
| 11,207,143 B2 * | 12/2021 | Abbott | ................... | A61B 34/30 |
| 11,337,769 B2 * | 5/2022 | Johnson | ................ | B25J 9/0009 |
| 2003/0221504 A1 | 12/2003 | Stoianovici et al. | | |
| 2007/0173789 A1 * | 7/2007 | Schena | .................. | A61B 34/37 606/1 |
| 2008/0187676 A1 * | 8/2008 | Blankenship | ........ | B25J 17/0266 427/446 |
| 2009/0012534 A1 * | 1/2009 | Madhani | ................ | B25J 9/1689 606/130 |
| 2009/0240259 A1 | 9/2009 | Nelson et al. | | |
| 2010/0160929 A1 * | 6/2010 | Rogers | ................... | A61B 34/30 606/130 |
| 2010/0204713 A1 * | 8/2010 | Ruiz Morales | .......... | B25J 9/041 606/130 |
| 2011/0213383 A1 * | 9/2011 | Lee | ........................ | A61B 34/71 606/130 |
| 2012/0227531 A1 * | 9/2012 | Subramanian | ..... | G02B 23/2476 901/18 |
| 2013/0144307 A1 * | 6/2013 | Jeong | ..................... | A61B 34/37 606/130 |
| 2014/0276952 A1 * | 9/2014 | Hourtash | ............... | B25J 9/1666 700/263 |
| 2014/0330288 A1 | 11/2014 | Date et al. | | |
| 2015/0025549 A1 | 1/2015 | Kilroy et al. | | |
| 2016/0235490 A1 * | 8/2016 | Srivastava | ............ | A61B 34/30 |
| 2016/0249993 A1 | 9/2016 | Farahmand et al. | | |
| 2017/0020615 A1 * | 1/2017 | Koenig | .................. | A61B 34/72 |
| 2018/0049737 A1 * | 2/2018 | Swayze | ........... | A61B 17/07207 |
| 2019/0231461 A1 * | 8/2019 | Steger | .................... | A61B 90/50 |
| 2019/0249759 A1 * | 8/2019 | Abbott | ................... | B25J 9/1689 |
| 2020/0315721 A1 * | 10/2020 | Rabindran | ............ | A61B 34/77 |
| 2020/0367982 A1 * | 11/2020 | Abbott | ................... | B25J 9/1689 |
| 2021/0244489 A1 * | 8/2021 | Lim | ........................ | B25J 18/00 |
| 2021/0378769 A1 * | 12/2021 | Zhou | ..................... | A61B 34/35 |

FOREIGN PATENT DOCUMENTS

| | | |
|---|---|---|
| EP | 1815950 A1 | 8/2007 |
| EP | 1951139 A2 | 8/2008 |
| EP | 2934361 A1 | 10/2015 |
| WO | WO-2013181522 A1 | 12/2013 |
| WO | WO-2013181526 A1 | 12/2013 |
| WO | WO-2015142788 A1 | 9/2015 |
| WO | WO-2015175200 A1 | 11/2015 |
| WO | WO-2016009301 A2 | 1/2016 |
| WO | WO-2016043845 A1 | 3/2016 |
| WO | WO-2016064616 A1 | 4/2016 |
| WO | WO-2016090459 A1 | 6/2016 |
| WO | WO-2016144998 A1 | 9/2016 |
| WO | WO-2016183054 A1 | 11/2016 |

OTHER PUBLICATIONS

Extended European Search Report for Application No. EP17862441.7 dated May 18, 2020, 10 pages.
International Search Report and Written Opinion for Application No. PCT/US2017/051846, dated Jan. 10, 2018, 11 pages.
International Search Report and Written Opinion for Application No. PCT/US2017/056990, dated Jan. 19, 2018, 11 pages.
Long J.A., et al., "Development of Miniaturized Light Endoscopeholder Robot for Laparoscopic Surgery," Journal of Endourology, Aug. 2007, vol. 21 (8), pp. 911-914.
Vertut, Jean and Phillips Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

COMPUTER-ASSISTED TELEOPERATED SURGERY SYSTEMS AND METHODS

CROSS-REFERENCE TO RELATED APPLICATIONS

This application is a National Stage Application under 35 U.S.C. § 371 and claims the benefit of International Application No. PCT/US2017/056990, filed Oct. 17, 2017, which claims the benefit of priority to U.S. Provisional Patent Application No. 62/409,625 (filed Oct. 18, 2016), the disclosures of which are incorporated herein by reference.

COPYRIGHT NOTICE

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT

Not Applicable.

BACKGROUND

1. Field of Invention

This disclosure relates to devices and methods for minimally invasive computer-assisted teleoperated surgery. For example, this disclosure provides manipulator devices for a computer-assisted teleoperated surgery system.

2. Art

Teleoperated surgical systems (often called "robotic" surgical systems because of the use of robot technology) and other computer-assisted devices often include one or more instrument manipulators to manipulate instruments for performing a task at a surgical work site and at least one manipulator for supporting an image capturing device which captures images of the surgical work site. A manipulator arm comprises a plurality of links coupled together by one or more actively controlled joints. In many embodiments, a plurality of actively controlled joints may be provided. The robot arm may also include one or more passive joints, which are not actively controlled, but which comply with movement of an actively controlled joint. Such active and passive joints may be various types, including revolute or prismatic joints. The kinematic pose of the manipulator arm and its associated instrument or image capture device may be determined by the positions of the joints and knowledge of the structure and coupling of the links and the application of known kinematic calculations.

Minimally invasive telesurgical systems for use in surgery are being developed to increase a surgeon's dexterity as well as to allow a surgeon to operate on a patient from a remote location. Telesurgery is a general term for surgical systems in which the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a stereoscopic image of the surgical site that provides the illusion of depth on a suitable viewer or display, the surgeon performs the surgical procedures on the patient by manipulating master control input devices, which in turn control the motion of corresponding teleoperated instruments. The teleoperated surgical instruments can be inserted through small, minimally invasive surgical apertures or natural orifices to treat tissues at surgical sites within the patient, often avoiding the trauma generally associated with accessing a surgical worksite by open surgery techniques. These computer-assisted tele-operated systems can move the working ends (end effectors) of the surgical instruments with sufficient dexterity to perform quite intricate surgical tasks, often by pivoting shafts of the instruments at the minimally invasive aperture, sliding of the shaft axially through the aperture, rotating of the shaft within the aperture, and the like.

SUMMARY

This disclosure provides devices and methods for minimally invasive robotic surgery using a computer-assisted tele-operated surgery device. For example, this disclosure provides manipulator devices for a computer-assisted tele-operated surgery system. In some embodiments, the manipulator device includes a first link that couples with a set-up structure, a second link that is rotatably coupled to the first link, and a third link that is pivotably coupled to the second link. The third link is configured to receive a surgical instrument actuator that can, in turn, receive a surgical instrument. The surgical instrument defines an insertion axis. In some such embodiments, pivoting the third link in relation to the second link causes a sweeping motion of the insertion axis that traces a portion of a conical surface. In some such embodiments, the manipulator device has a hardware-constrained remote center of motion (RCM). The RCM is a point in space around which the roll, pitch, and yaw motions of the manipulator device are made. When the manipulator devices are used for minimally invasive computer-assisted teleoperated surgery, movement of the manipulator assembly is constrained to a safe motion through a minimally invasive surgical access site or other aperture that is substantially coincident with the RCM. The motion of the manipulator device will thereby preclude excessive lateral motion of the body wall access cannula which might otherwise tear the tissues adjacent the aperture or enlarge the access site inadvertently.

In one aspect, this disclosure is directed to a computer-assisted tele-operated surgery manipulator device that includes a first link configured to releasably couple with a set-up structure of a computer-assisted tele-operated surgery system; a second link rotatably coupled to the first link such that the second link is rotatable in relation to the first link about a first axis; and a third link pivotably coupled to the second link such that the third link is pivotable in relation to the second link about a second axis. The third link is configured to releasably couple with a patient body wall access cannula defining an insertion axis for a surgical instrument. The first axis, the second axis, and the insertion axis consistently intersect at a particular fixed point in space throughout rotation of the second link in relation to the first link and pivoting of the third link in relation to the second link. Pivoting the third link in relation to the second link sweeps the insertion axis to trace a portion of a conical surface.

Such a computer-assisted tele-operated surgery manipulator device may optionally include one or more of the following features. The second link may include a leadscrew, a motor for rotating the leadscrew, and a nut threadably coupled to the leadscrew. The nut may be coupled to a linkage pivotably coupled to the third link at a location spaced apart from the second axis. Rotation of the leadscrew may cause the third link to pivot in relation to the second link. The third link may be releasably coupleable with a computer-assisted teleoperated surgical instrument actuator. The third link may include a motor for driving rotations of the computer-assisted tele-operated surgical instrument actuator about the insertion axis. The first link may include a motor that drives rotations of the second link in relation to the first link. In some embodiments, throughout rotation of the second link in relation to the first link and pivoting of the third link in relation to the second link, the second axis may remain non-orthogonal to the insertion axis. In some embodiments, during surgery using the computer-assisted teleoperated surgery manipulator device and at all positions of the third link in relation to the second link, the second link may be rotated in relation to the first link through an arc of at least 120 degrees without contact between the manipulator device and a plane that includes the particular fixed point in space. In particular embodiments, during surgery using the computer-assisted tele-operated surgery manipulator device the first axis may be at an angle of less than 30 degrees in relation to the plane that includes the particular fixed point in space.

In another aspect, this disclosure is directed to a computer-assisted teleoperated surgery manipulator device including: a first link configured to releasably couple with a set-up structure of a computer-assisted tele-operated surgery system; a second link rotatably coupled to the first link such that the second link is rotatable in relation to the first link about a first axis, the second link comprising a leadscrew and a nut threadably coupled to the leadscrew; and a third link pivotably coupled to the second link such that the third link is pivotable in relation to the second link about a second axis. The third link is configured to releasably couple with a patient body wall access cannula defining an insertion axis for a surgical instrument. The first axis, the second axis, and the insertion axis consistently intersect at a particular fixed point in space throughout rotation of the second link in relation to the first link and pivoting of the third link in relation to the second link. The nut is coupled to a linkage that is pivotably coupled to the third link at a location spaced apart from the second axis, and wherein rotation of the leadscrew causes the third link to pivot in relation to the second link.

Such a computer-assisted teleoperated surgery manipulator device may optionally include one or more of the following features. The insertion axis may trace a portion of a conical surface as the third link is pivoted in relation to the second link. The third link may be releasably coupleable with a computer-assisted tele-operated surgical instrument actuator. The third link may include a motor for driving rotations of the computer-assisted teleoperated surgical instrument actuator about the insertion axis. The first link may include a motor that drives rotations of the second link in relation to the first link. Throughout rotation of the second link in relation to the first link and pivoting of the third link in relation to the second link, the second axis may remain non-orthogonal to the insertion axis. During surgery using the computer-assisted tele-operated surgery manipulator device and at all positions of the third link in relation to the second link, the second link may be rotatable in relation to the first link through an arc of at least 120 degrees without contact between the manipulator device and a plane that includes the particular fixed point in space. In some embodiments, during surgery using the computer-assisted teleoperated surgery manipulator device the first axis is at an angle of less than 30 degrees in relation to the plane that includes the particular fixed point in space.

In another aspect, this disclosure is directed to a computer-assisted teleoperated surgery system including: a set-up structure releasably coupleable with a frame; a manipulator device; and a computer-assisted tele-operated surgical instrument actuator releasably coupleable with the third link. The manipulator device includes: a first link configured to releasably couple with a set-up structure of a computer-assisted tele-operated surgery system; a second link rotatably coupled to the first link such that the second link is rotatable in relation to the first link about a first axis; and a third link pivotably coupled to the second link such that the third link is pivotable in relation to the second link about a second axis. The third link is configured to releasably couple with a patient body wall access cannula defining an insertion axis for a surgical instrument. The first axis, the second axis, and the insertion axis consistently intersect at a particular fixed point in space throughout rotation of the second link in relation to the first link and pivoting of the third link in relation to the second link. Pivoting the third link in relation to the second link sweeps the insertion axis to trace a portion of a conical surface. The third link includes a roll-adjustment motor that drives rotation of the surgical instrument actuator about the insertion axis.

Such a computer-assisted tele-operated surgery system may optionally include one or more of the following features. An entirety of the instrument actuator can be rotatably drivable by the roll-adjustment motor. The system may also include the computer-assisted teleoperated surgical instrument receivable by the surgical instrument actuator. The second link may include a leadscrew, a motor for rotating the leadscrew, and a nut threadably coupled to the leadscrew. The nut may be coupled to a linkage that is pivotably coupled to the third link at a location spaced apart from the second axis. Rotation of the leadscrew causes the third link to pivot in relation to the second link. In some embodiments, during surgery using the computer-assisted teleoperated surgery manipulator device and at all positions of the third link in relation to the second link, the second link may be rotated in relation to the first link through an arc of at least 120 degrees without contact between the manipulator device and a plane that includes the particular fixed point in space.

Some or all of the embodiments described herein may provide one or more of the following advantages. In some cases, the teleoperated surgical manipulator devices provided herein are advantageously structured to have a low-profile, i.e., to be spatially-compact and/or able to be oriented at a low angle (e.g., in a range of about 15° to about 30°) to the patient. Such a compact configuration is advantageous in that the working space occupied by the teleoperated surgical manipulators above the patient is minimized, allowing for enhanced patient access by the surgical team. Additionally, greater visualization of the patient and communications between the surgical team members is facilitated by the compact manipulator working space.

Further, lessening the size of the manipulator working space can reduce the potential for collisions between manipulators. In result, the need for redundant degrees of freedom of the manipulators is mitigated. Hence, the complexity of the manipulators can be lessened in some cases.

The compact size of the tele-operated surgical manipulator devices provided herein can also advantageously facilitate mounting the manipulators to a rail of an operating table in some cases. In such a case, as the operating table is manipulated to enhance surgical access, the table-mounted manipulator devices inherently follow. Therefore, the need to reposition the manipulators in response to movements of the operating table is advantageously reduced or eliminated.

In addition, the teleoperated surgical manipulator devices provided herein are advantageously structured to have a relatively low mass and inertia. In addition, the mass distribution is substantially constant such that the inertia is substantially constant, and therefore predictable.

The details of one or more embodiments are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 2:
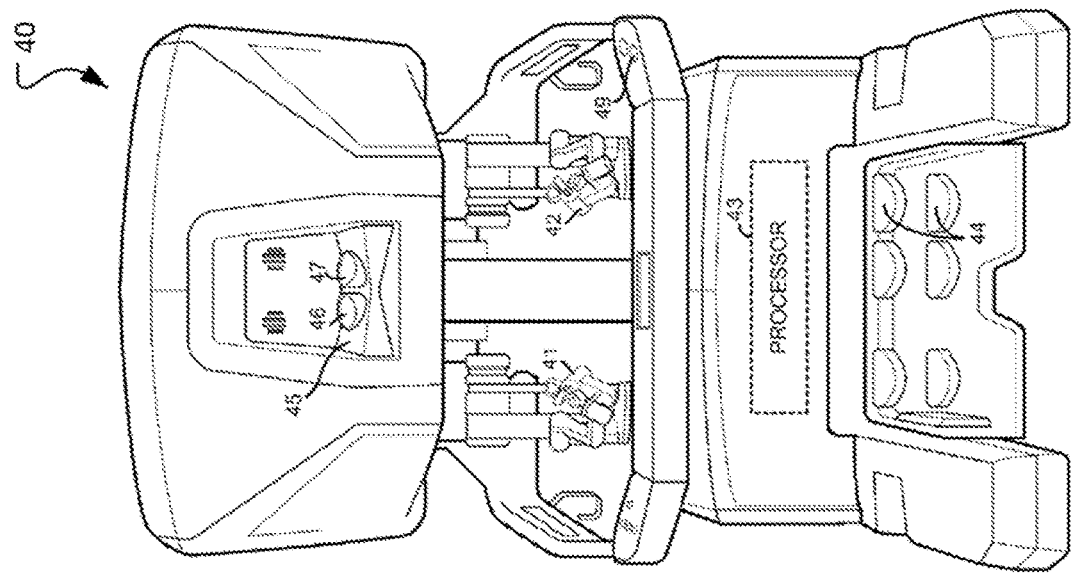
FIG. 2 is a front view of an example surgeon console of a computer-assisted tele-operated surgery system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different locations (i.e., translational placements) and orientations (i.e., rotational placements) of a device in use or operation in addition to the location and orientation shown in the figures. For example, if a device in the figures is turned over, elements described as "below" or "beneath" other elements or features would then be "above" or "over" the other elements or features. Thus, the exemplary term "below" can encompass both locations and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device locations and orientations. The combination of a body's location and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, each of the one or more individual listed items should be considered optional unless otherwise stated, so that various combinations of items are described without an exhaustive list of each possible combination. The auxiliary verb may likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

An example of a teleoperated surgical system is the da Vinci® Surgical System, commercialized by Intuitive Surgical, Inc. of Sunnyvale, Calif. Inventive aspects are associated with computer-assisted teleoperated surgical systems. Knowledgeable persons will understand that inventive aspects disclosed herein may be embodied and implemented in various ways, including computer-assisted and hybrid combinations of manual and computer-assisted embodiments and implementations. As applicable, inventive aspects may be embodied and implemented in both relatively smaller, hand-held, hand-operated devices and relatively larger systems that have additional mechanical support, as well as in other embodiments of computer-assisted tele-operated medical devices. In addition, inventive aspects are associated with advances in computer-assisted surgical systems that include autonomous rather than teleoperated actions, and so both teleoperated and autonomous surgical systems are included, even though the description concentrates on teleoperated systems.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller", encompasses both centralized single-location and distributed implementations.

This disclosure provides improved surgical and telesurgical devices, systems, and methods. The inventive concepts are particularly advantageous for use with telesurgical systems in which a plurality of surgical tools or instruments are mounted on and moved by an associated plurality of teleoperated manipulators during a surgical procedure. The teleoperated surgical systems will often comprise tele-robotic, telesurgical, and/or telepresence systems that include processors configured as master-slave controllers. By providing teleoperated surgical systems employing processors appropriately configured to move manipulator assemblies with articulated linkages having relatively large numbers of degrees of freedom, the motion of the linkages can be tailored for work through a minimally invasive access site. The large number of degrees of freedom may also allow a processor to position the manipulators to inhibit interference or collisions between these moving structures, and the like.

The manipulator assemblies described herein will often include a teleoperated manipulator and a tool mounted thereon (the tool often comprising a surgical instrument in surgical versions), although the term "manipulator assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base that is fixed in space during at least a portion of a telesurgical procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. As used herein, the term "end effector" therefore includes but is not limited to the function of changing the orientation or position (e.g., a "wrist" function, a parallel motion function) of its distal-most part or parts (e.g., jaw(s) and the like).

When used for minimally invasive teleoperated surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the manipulator motion at the access site may be imposed using mechanical manipulator joint linkages that inhibit improper motions, or may in part or in full be imposed using robotic data processing and control techniques. Hence, such minimally invasive aperture-constrained motion of the manipulator assembly may employ between zero and three degrees of freedom of the manipulator assembly.

Many of the exemplary manipulator assemblies described herein will have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly.

Figure 1:
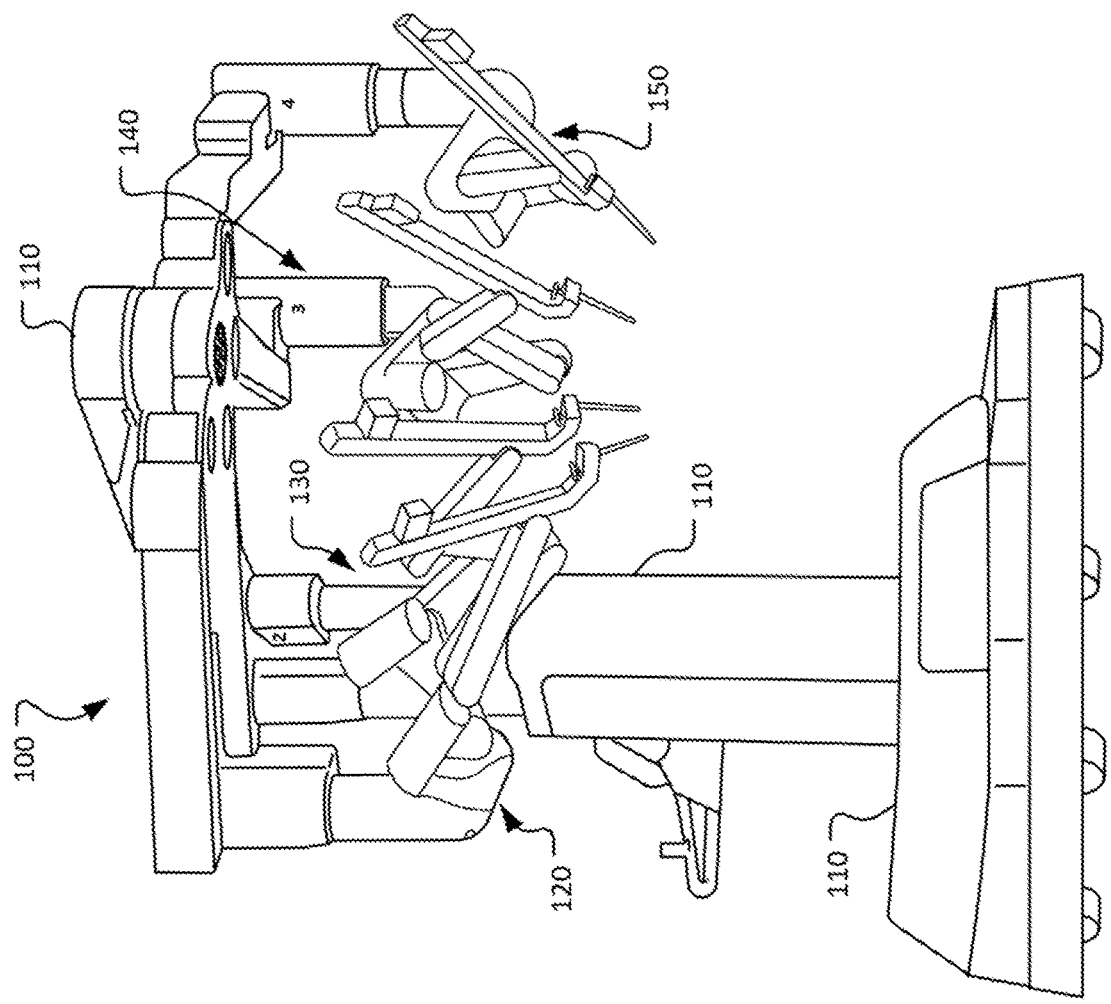
FIG. 1 is a perspective view of an example patient-side cart of a computer-assisted tele-operated surgery system.

Referring to FIGS. 1 and 2, systems for minimally invasive computer-assisted telesurgery (as referred to herein as "minimally invasive robotic surgery") can include a patient-side unit 100 and a surgeon control unit 40. Telesurgery is a general term for surgical systems where the surgeon uses some form of remote control, e.g., a servomechanism, or the like, to manipulate surgical instrument movements by using robot technology rather than directly holding and moving the instruments by hand. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side unit 100 includes a base 110, a first robotic manipulator arm assembly 120, a second robotic manipulator arm assembly 130, a third robotic manipulator arm assembly 140, and a fourth robotic manipulator arm assembly 150. As shown, the base 110 includes a portion that rests on the floor, a vertical column, and a horizontal boom, and other base configurations to mechanically ground the patient-side unit may optionally be used. Each robotic manipulator arm assembly 120, 130, 140, and 150 is pivotably coupled to the base 110. In some embodiments, fewer than four or more than four robotic manipulator arm assemblies may be included as part of the patient-side unit 100. While in the depicted embodiment the base 110 includes casters to allow ease of mobility, in some embodiments the patient-side unit 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device (tool; surgical instrument) so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces 46 and 47 are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals. Additional input to the system may be made via one or more other inputs, such as buttons, touch pads, voice, and the like, as illustrated by input 49.

A processor 43 is provided in the surgeon console 40 for control and other purposes. The processor 43 performs various functions in the medical robotic system. One function performed by processor 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processor 43 is to implement the methods, cross-coupling control logic, and controllers described herein.

Although described as a processor, it is to be appreciated that the processor 43 may be implemented by any combination of hardware, software, and firmware. Also, its functions as described herein may be performed by one unit or divided up among a number of subunits, each of which may be implemented in turn by any combination of hardware, software, and firmware. Further, although being shown as part of or being physically adjacent to the surgeon control unit 40, the processor 43 may also be distributed as subunits throughout the telesurgery system. Accordingly, control aspects referred to herein are implemented via processor 43 in either a centralized or distributed form.

Figure 3:
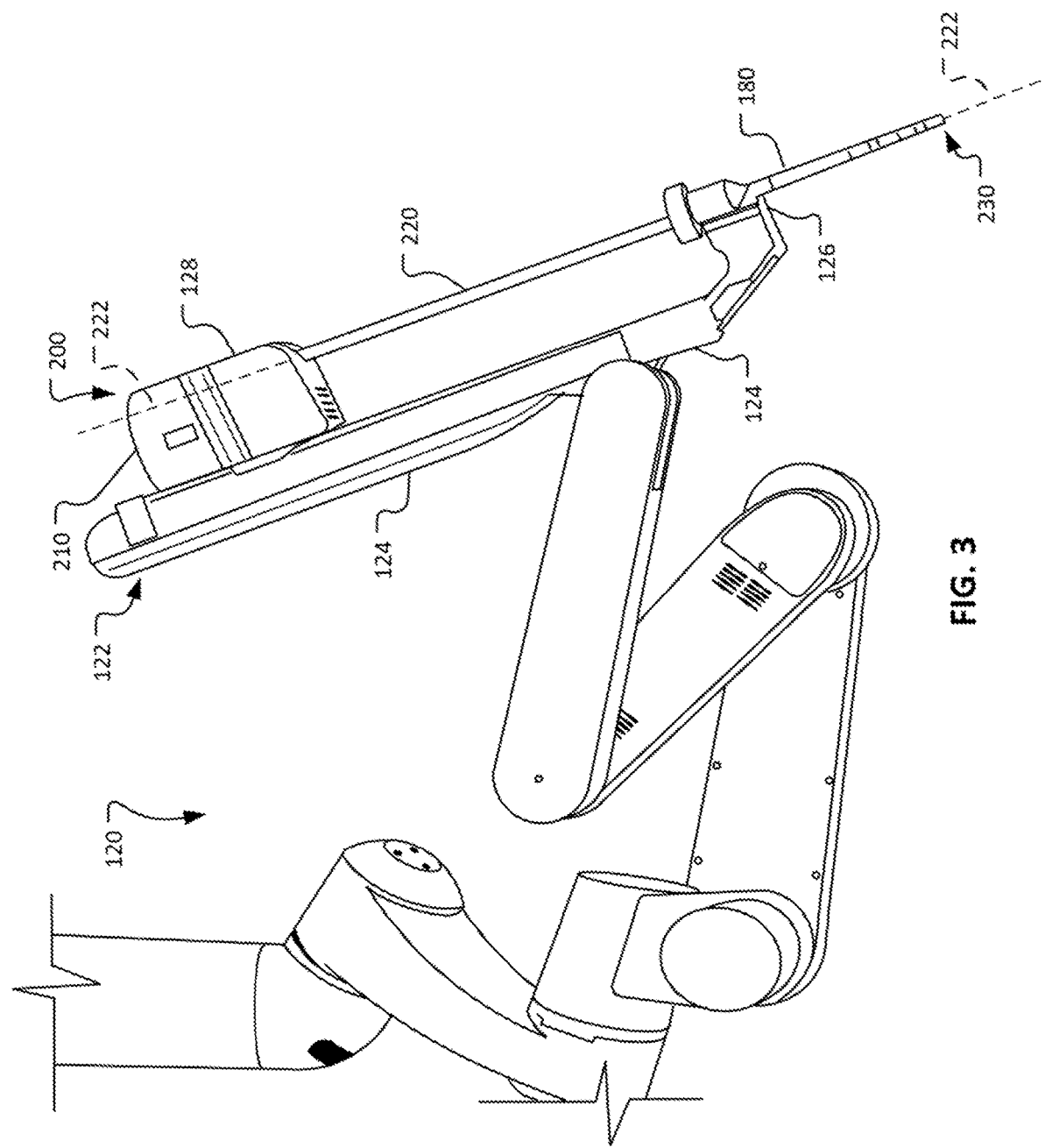
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as surgical instruments to perform minimally invasive surgery. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member.

The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43.

The surgical instrument 200 includes a transmission assembly 210, the elongate shaft 220, and an end effector 230. The transmission assembly 210 is releasably coupleable with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 4:
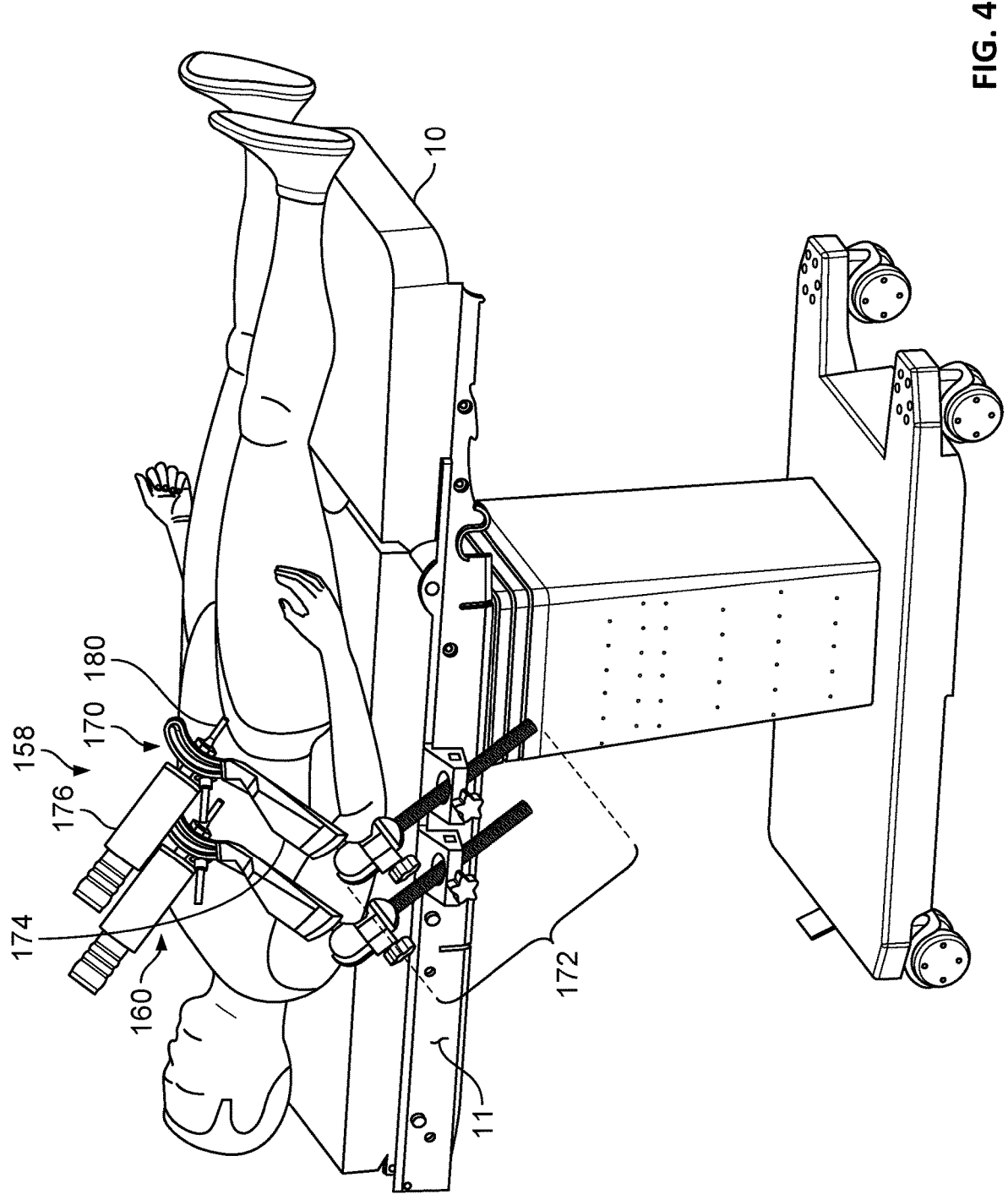
FIG. 4 is a perspective view of another type of patient-side computer-assisted tele-operated surgery system.

Also referring to FIG. 4, another example patient-side system 160 for minimally invasive computer-assisted tele-operated surgery includes a first robotic manipulator arm assembly 162 and a second robotic manipulator arm assembly 164 that are each mounted to an operating table 10. In some cases, this configuration of patient-side system 160 can be used as an alternative to the patient-side unit 100 of FIG. 1. While only two robotic manipulator arm assemblies 162 and 164 are depicted, it should be understood that more than two (e.g., three, four, five, six, and more than six) can be included in some configurations.

In some cases, the operating table 10 may be moved or reconfigured during the surgery. For example, in some cases, the operating table 10 may be tilted about various axes, raised, lowered, pivoted, rotated, and the like. In some cases, by manipulating the orientation of the operating table 10, the clinicians can utilize the effects of gravity to position internal organs of the patient in positions that facilitate enhanced surgical access. In some cases, such movements of the operating table 10 may be integrated as a part of the computer-assisted tele-operated surgery system, and controlled by the system.

Figure 5:
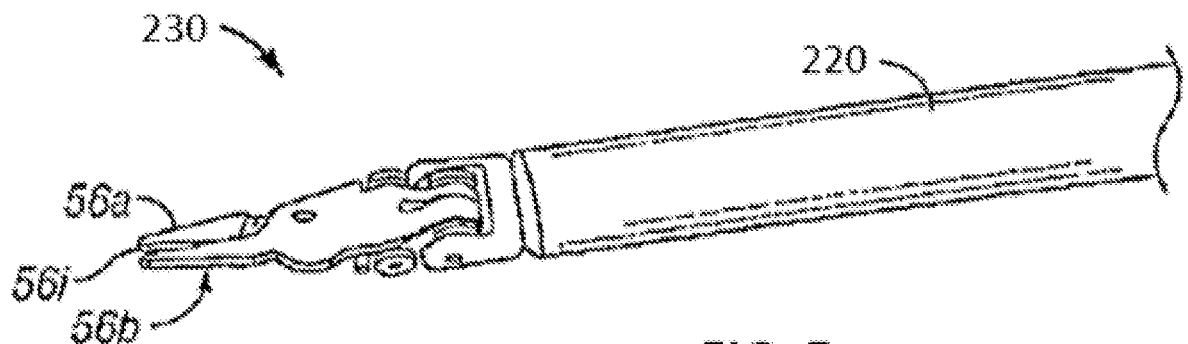
FIG. 5 is a perspective view of a distal end portion of an example surgical instrument in a first configuration.
Figure 6:
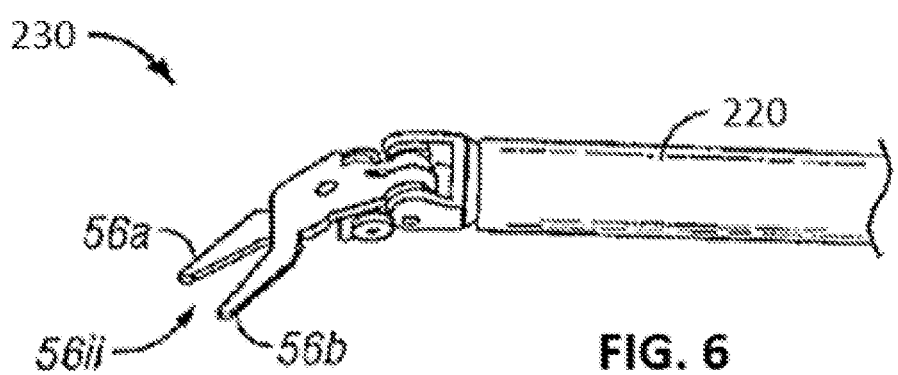
FIG. 6 is a perspective view of the distal end portion of the surgical instrument of FIG. 5 in a second configuration.
Figure 7:
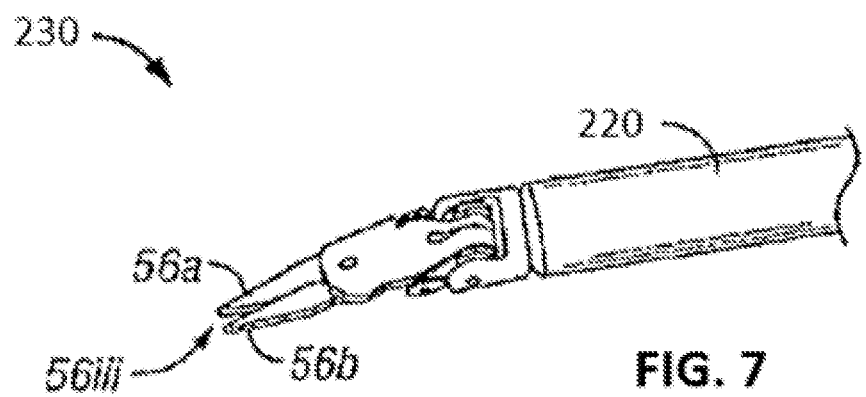
FIG. 7 is a perspective view of the distal end portion of the surgical instrument of FIG. 5 in a third configuration.

Also referring to FIGS. 5-7, a variety of alternative computer-assisted tele-operated surgical instruments of different types and differing end effectors 230 may be used, with the instruments of at least some of the manipulators being removed and replaced during a surgical procedure. Several of these end effectors, including, for example, DeBakey Forceps 56*i*, microforceps 56*ii*, and Potts scissors 56*iii* include first and second end effector elements 56*a*, 56*b* which pivot relative to each other so as to define a pair of end effector jaws. Other end effectors, including scalpels and electrocautery probes, have a single end effector element. For instruments having end effector jaws, the jaws will often be actuated by squeezing the grip members of input devices 41, 42.

In some cases, the computer-assisted tele-operated surgical instruments include multiple degrees of freedom such as, but not limited to, roll, pitch, yaw, insertion depth, opening/closing of jaws, actuation of staple delivery, activation of electro-cautery, and the like. At least some of such degrees of freedom can be actuated by an instrument drive system to which the surgical instrument can be selectively coupled.

In some embodiments, the computer-assisted tele-operated surgical instruments include end effectors with two individually movable components such as, but not limited to, opposing jaws designed for grasping or shearing. When a first one of the individually movable components is moved as a second one of the individually movable components remains generally stationary or is moved in an opposing manner, the end effector can perform useful motions such as opening and closing for grasping, shearing, releasing, and the like. When the two components are moved synchronously in the same direction, speed and distance, the resulting motion is a type of pitch or yaw movement of the end effector. Hence, in some surgical instrument embodiments that have end effectors with two individually movable components, such as jaws, the arrangement can provide two degrees of freedom (e.g., pitch/yaw movements and opening/closing movements).

The elongate shaft 220 allow the end effector 230 and the distal end of the shaft 220 to be inserted distally into a surgical worksite through a minimally invasive aperture (via cannula 180), often through a body wall (e.g., abdominal wall) or the like. In some cases, a body wall retractor member on a distal end of the cannula 180 can be used to tent the body wall, thereby increasing the surgical workspace size. In some cases the surgical worksite may be insufflated, and movement of the end effectors 230 within the patient will often be effected, at least in part, by pivoting of the instruments 200 about the location at which the shaft 220 passes through the minimally invasive aperture. In other words, the robotic manipulator arm assemblies 120, 130, 140, and 150 will move the transmission assembly 210 outside the patient so that the shaft 220 extends through a minimally invasive aperture location so as to help provide a desired movement of end effector 50. Hence, the robotic manipulator arm assemblies 120, 130, 140, and 150 will often undergo significant movement outside patient during a surgical procedure.

Figure 8:
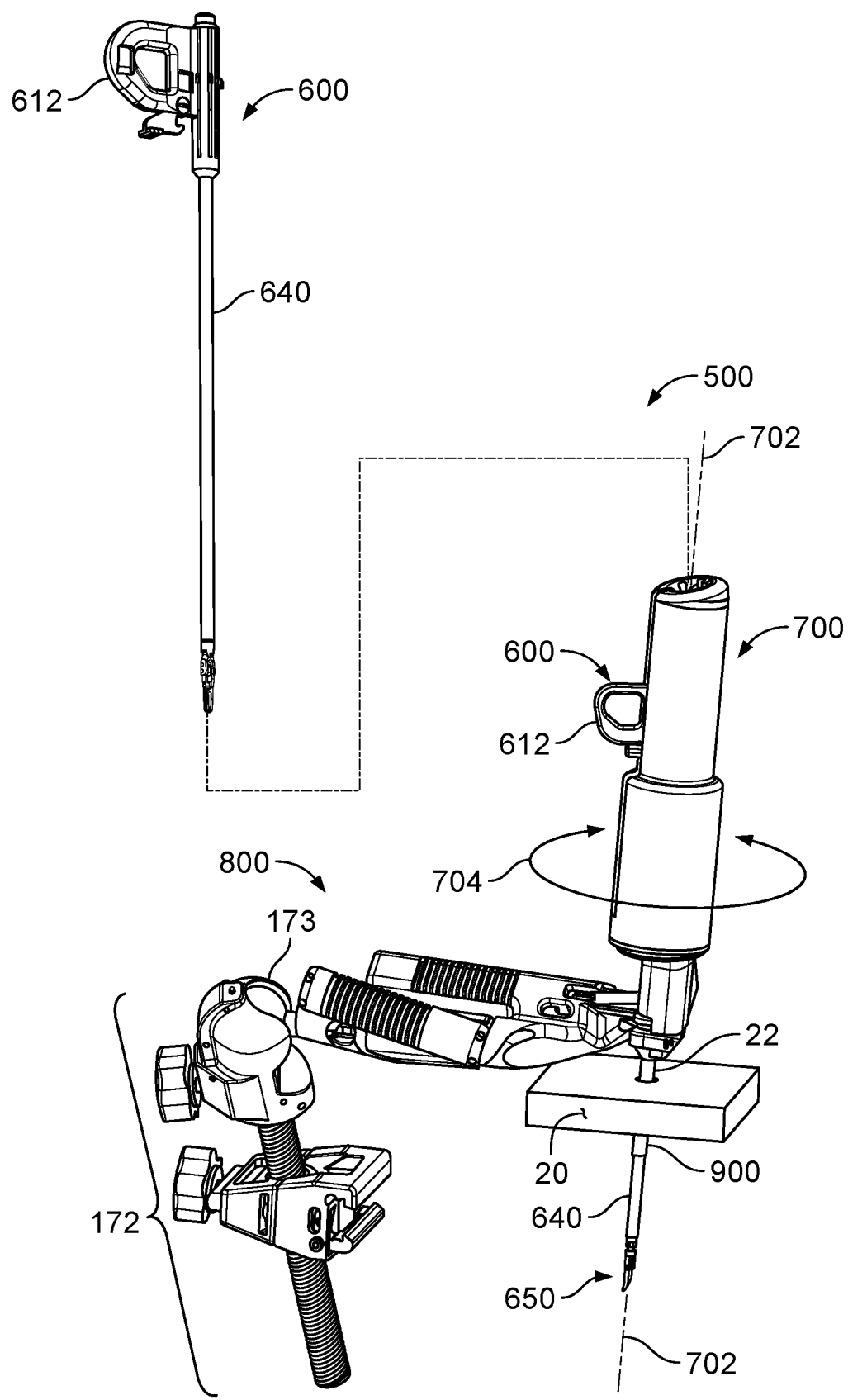
FIG. 8 is a perspective view depicting a surgical instrument coupled with a surgical instrument actuation pod that is mounted to an example computer-assisted tele-operated surgery manipulator device in accordance with some embodiments.

Referring to FIG. 8, an example computer-assisted teleoperated surgery system 500 (a "telesurgical system") is shown in relation to a portion of a simulated patient body wall 20. The system 500 includes the set-up structure 172, a manipulator device 800, which is an assembly that includes a surgical instrument actuator 700, a surgical instrument 600, and a cannula 900.

The set-up structure 172 can be adjustably mounted to a base or frame (i.e., a mechanical ground) such as, but not limited to, a bed rail of an operating room table. The manipulator device assembly 800 is releasably and adjustably coupleable with the set-up structure 172. In some embodiments, the set-up structure 172 and the manipulator device assembly 800 can be manually adjusted and then locked into a desired pose of a multitude of possible poses in relation to the patient's body wall 20. For example, the set-up structure 172 and the manipulator device assembly 800 can be manually adjusted so that the cannula 900 is aligned with a surgical access location 22. Such adjustments can be made prior to initiation of a surgery or during a surgery.

The manipulator device assembly 800 includes releasably coupleable compatible surgical instrument actuator 700 (also referred to herein as a "surgical instrument actuation pod," or a simply a "pod"). In some embodiments, the pod 700 is readily detachable from the manipulator assembly 800 such that the pod 700 can be conveniently interchanged with another pod. The pod 700 defines an insertion axis 702 along which a surgical instrument is inserted and withdrawn. In some embodiments, the manipulator device assembly 800 can rotatably drive an entirety of the pod 700 (and the surgical instrument 600 coupled with the pod 700) to rotate at a revolute roll joint about the insertion axis 702 as depicted by arrow 704. Such motion may be referred to as roll motion or simply "roll."

When the surgical instrument 600 is coupled with the pod 700, a shaft 640 of the surgical instrument 600 slidably extends through the cannula 900, which is releasably coupled with the manipulator assembly 800. In use, the cannula 900 can extend through the body wall 20 of the patient at the surgical access location 22 (which can be defined by a trocar, a port, an incision, a natural body orifice, and the like). The surgical instrument 600 includes an end effector 650 that is controlled by the surgeon performing the computer-assisted teleoperated surgery.

The pod 700 defines a space configured to receive the surgical instrument 600. When the surgical instrument 600 is coupled with the pod 700, the pod 700 can actuate movements of the end effector 650 and of the surgical instrument 600 as a whole. For example, the pod 700 can actuate translational movements of the surgical instrument 600 along the longitudinal insertion axis 702 of the pod 700. That is, the pod 700 can insert and retract the surgical instrument 600 deeper (distally) and shallower (proximally) in relation to the patient. Hence, the longitudinal axis 702 is sometimes also referred to as the insertion axis 702.

Figure 9:
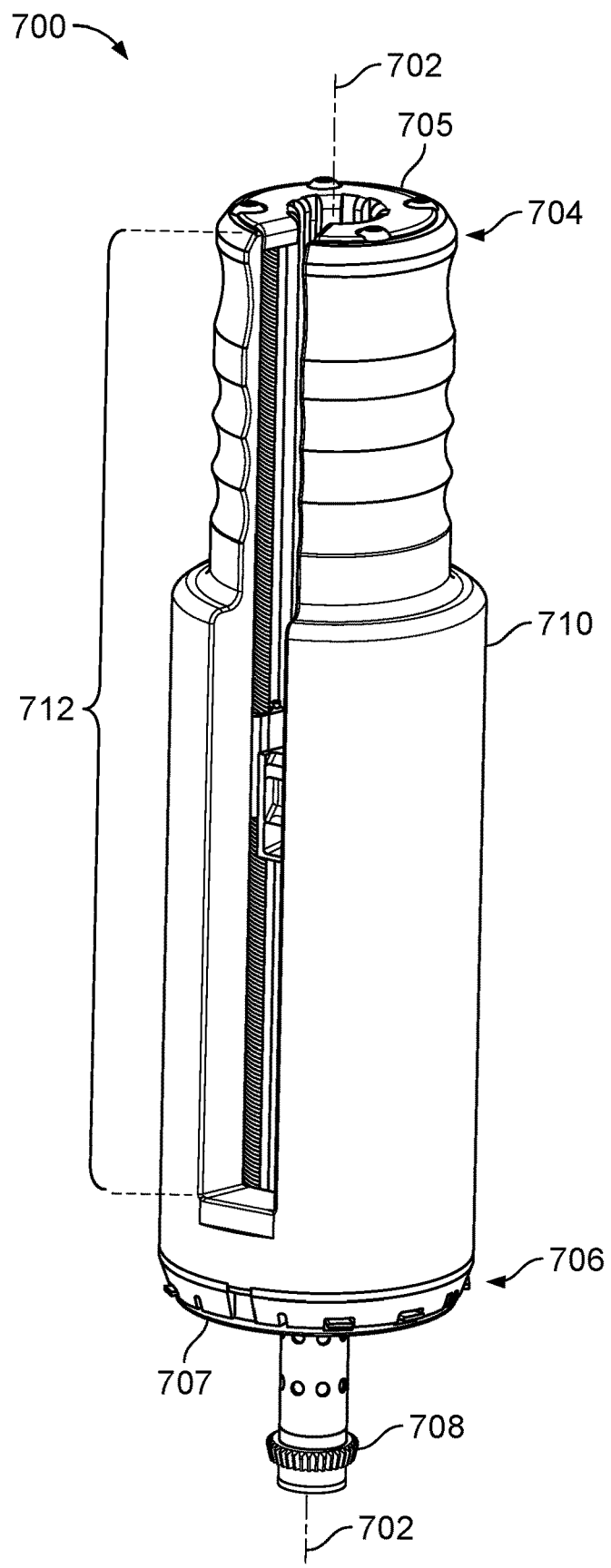
FIG. 9 is a perspective view of an example surgical instrument actuation pod in accordance with some embodiments.

Referring also to FIG. 9, the example surgical instrument actuator pod 700 is shown in isolation from the surgical instrument 600 and the manipulator device assembly 800. The pod 700 includes a proximal end 704 and a distal end 706. The proximal and distal ends of the pod 700 define the longitudinal axis 702 along which a surgical instrument (or other device such as an endoscopic camera) can be installed.

In the depicted embodiment, the pod 700 includes a proximal end plate 705, a distal end plate 707, and a housing 710. The housing 710 extends between the proximal end 704 and the distal end 706.

In the depicted embodiment, the proximal end plate 705 is a C-shaped plate, while the distal end plate 707 is a fully circumferential plate that defines an open center. The opening in the proximal end plate 705 aligns with a slot opening 712 defined by the housing 710. The slot opening 712 and the opening in the C-shaped proximal end plate 705 provide clearance for a handle 612 of the surgical instrument 600 to project radially from the housing 710 while the surgical instrument 600 is coupled with the instrument drive system 700.

In the depicted embodiment, the pod 700 also includes a roll driven gear 708. The pod's roll driven gear 708 is positioned to mesh with and to be driven by a roll drive gear 847 (refer to FIGS. 10-12 and 16) coupled to a roll drive (roll-adjustment) motor 846 (FIG. 11) of a third link 830 of the manipulator device assembly 800 when the pod 700 is coupled with the instrument actuator coupling 840 of the manipulator device assembly 800. Roll drive gear 847 driven by motor 846 engages roll driven gear 708, and motor 846 and roll drive gear 847 are illustrative of various roll drive assemblies that may be used. When the roll driven gear 708 is so driven, the entire pod 700 rotates or rolls (as depicted by arrow 704, FIG. 8) about the insertion axis 702. When the surgical instrument 600 is engaged with the pod 700, the surgical instrument 600 also rotates or rolls about the insertion axis 702 correspondingly as the roll driven gear 708 is driven by the roll drive gear 847 of the instrument actuator coupling 840. Accordingly, insertion axis 702 also functions as an instrument roll axis around with elongate shaft 640 (FIG. 8) rolls.

Figure 10:
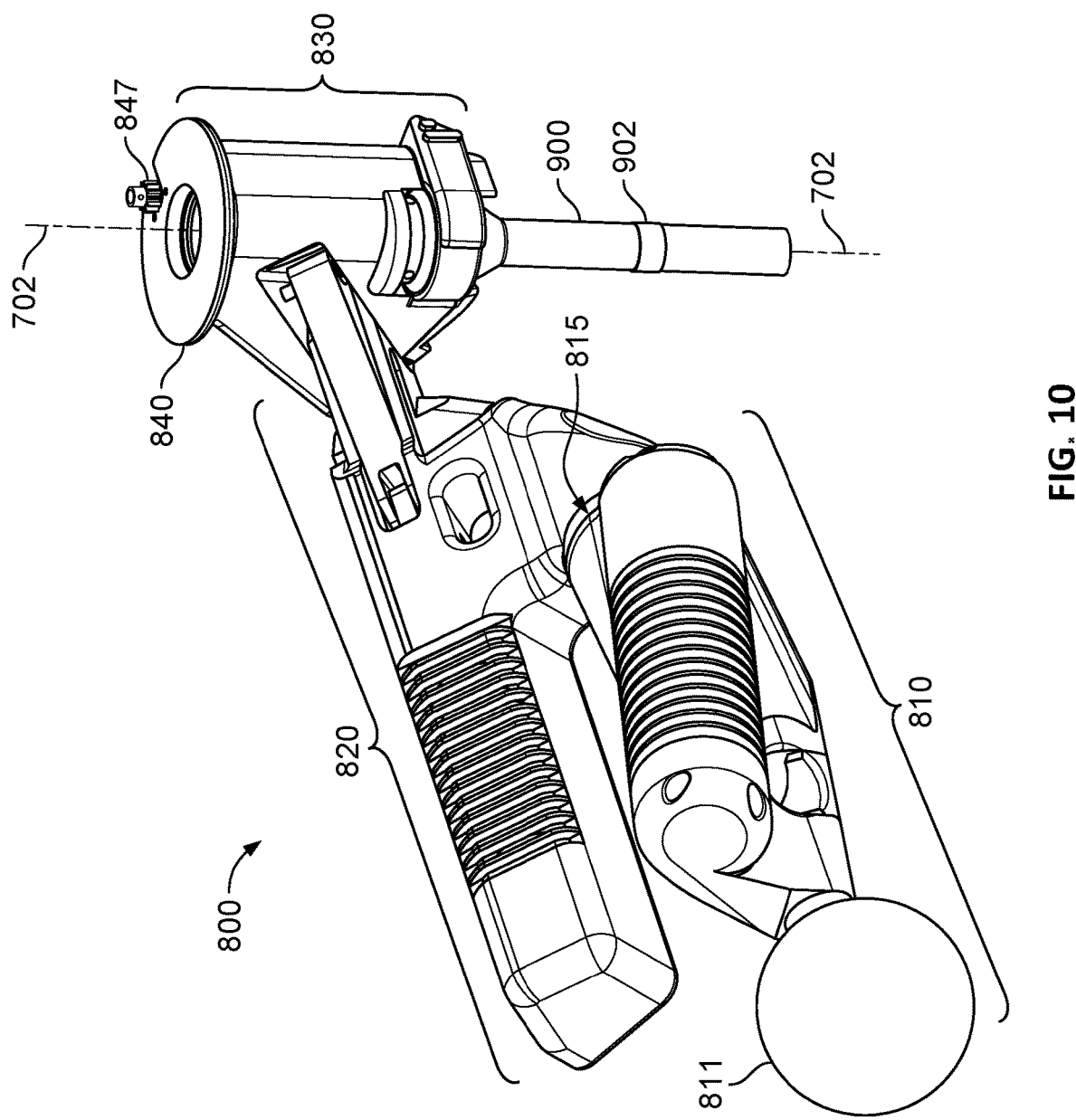
FIG. 10 is a perspective view of an example computer-assisted tele-operated surgery manipulator device in accordance with some embodiments.
Figure 11:
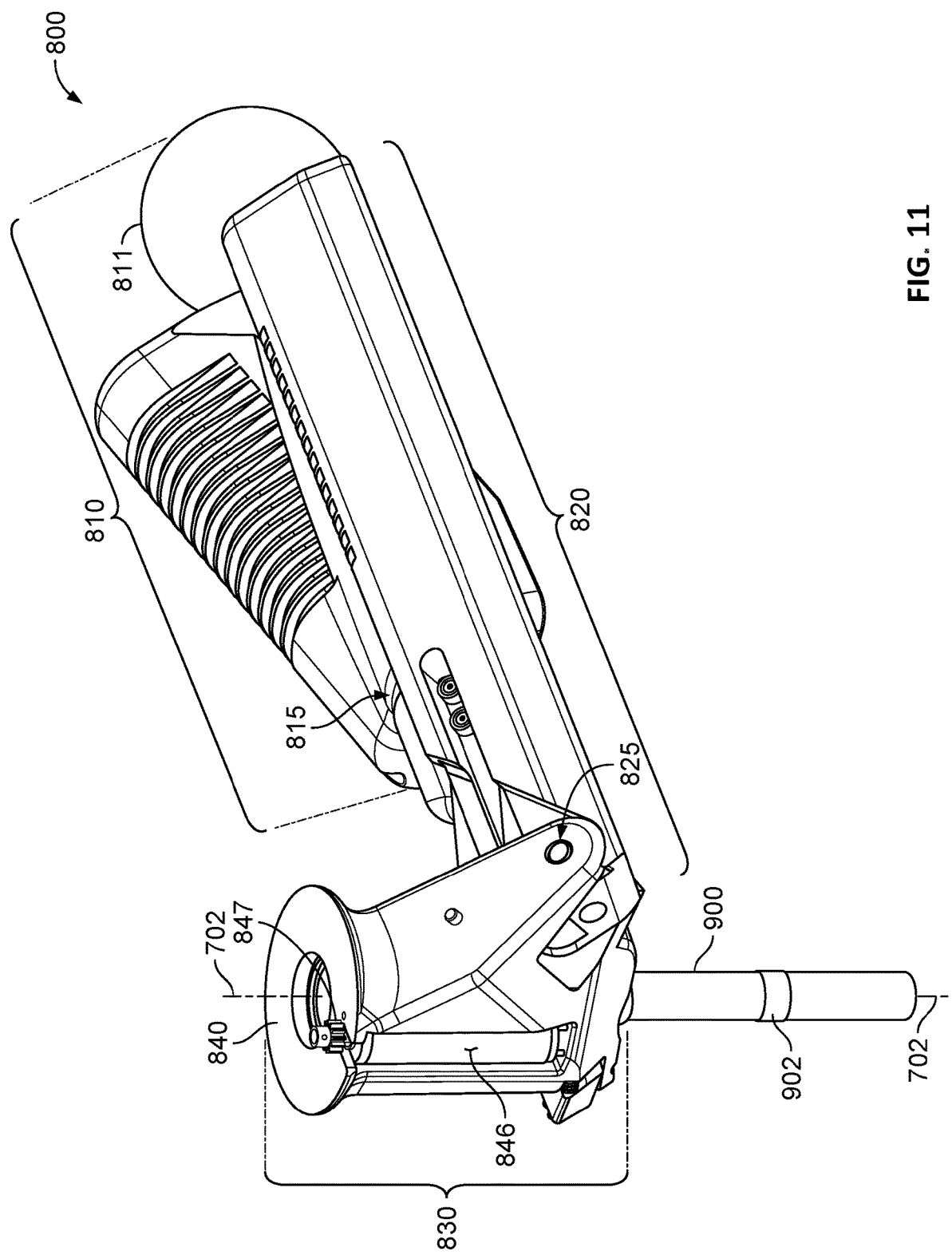
FIG. 11 is another perspective view of the manipulator device of FIG. 10.

Referring also to FIGS. 10 and 11, here a portion of the manipulator device assembly 800 is shown in isolation from the other devices of the computer-assisted teleoperated surgery system 500. The manipulator device assembly 800 includes a first link 810, a second link 820, and a third link 830. The first link 810 and the second link 820 are rotatably coupled. That is, as described further below, the second link 820 can be rotated in relation to the first link 810. The second link 820 and the third link 830 are rotatably coupled at a pivot. That is, as described further below, the third link 830 can be pivoted in relation to the second link 820.

The first link 810 is configured to releasably couple with the set-up structure 172. Accordingly, in the depicted embodiment the first link includes a ball 811 extending from a proximal end of the first link 810. The ball 811 is configured to be received in a socket 173 of the set-up structure 172. The ball-in-socket connection between the ball 811 and the socket 173 (a spherical joint) allows for orientation adjustability between the manipulator device assembly 800 and the set-up structure 172. When a desired orientation between the manipulator device 800 and the set-up structure 172 has been attained, the ball-in-socket connection between the ball 811 and the socket 173 can be releasably clamped in a fixed orientation. Thereafter, the first link 810 remains stationary in relation to the set-up structure 172 until the two are unclamped and readjusted.

The ball-in-socket connection is merely one non-limiting example of the types of mechanical connections that can be used between the manipulator device assembly 800 and the set-up structure 172. For example, articulating joints, x-y-z adjustment mechanisms, and the like, and combinations thereof, can be used. The connection between the manipulator device assembly 800 and the set-up structure 172 can be passive (manually adjustable) or active (power adjustable or power-assist adjustable).

The third link 830 is configured to releasably couple with the patient body wall access cannula 900 that is coaxial with the insertion axis 702. The cannula 900 defines a lumen that slidably receives the shaft 640 of the surgical instrument 600 (or of other devices such as, but not limited to, an endoscope) along the insertion axis 702. As shown in FIG. 8, the cannula 900 extends distally from the third link 830 through the patient's body wall 20 via the surgical access location 22.

As described further herein, in order to facilitate movements of the surgical instrument 600 (and of the end effector 650 in particular), the relative configuration of the links 810, 820, and 830 of the manipulator device assembly 800 actively adjust in response to input (e.g., surgeon input using the surgeon console 40 and processor 43 as described in reference to FIG. 2). It can be said, therefore, that the manipulator device assembly 800 is configured to actuate pitch, roll, and yaw motions of the surgical instrument 600 as a whole in response to actuation input. Moreover, as described further herein, the manipulator device assembly 800 is configured to actuate such pitch, roll, and yaw motions of the surgical instrument 600 without creating excessive lateral motion of the body wall access cannula 900, which might tend to stress or tear the tissues adjacent the surgical access location 22 or to enlarge the access site inadvertently.

In the depicted embodiment, the manipulator device assembly 800 is designed with a hardware-constrained remote center of motion (RCM) 902 so that pitch, roll, and yaw motions of the surgical instrument 600 as a whole can be implemented by the manipulator device 800 without creating excessive lateral motion of the body wall access cannula 900. The RCM 902 is a point in space around which the roll, pitch, and yaw motions described above are made. In the depicted embodiment, the RCM 902 is a point on the insertion axis 702 that is fixed at a particular longitudinal position along the cannula 900. As the relative configuration of the links 810, 820, and 830 of the manipulator device assembly 800 actively adjust in response to user input, the RCM 902 remains fixed in space. Therefore, while pitch, roll, and yaw motions of the surgical instrument 600 as a whole are implemented by the manipulator device 800, excessive lateral motion of the body wall access cannula 900 that might tend to stress or tear the tissues adjacent the surgical access location 22 or to enlarge the access site inadvertently is avoided. In some embodiments, the RCM can be located at other points (e.g., at a particular distance away from the insertion axis 702). In some embodiments, the manipulator device assembly 800 can be implemented using a software-constrained RCM rather than, or in addition to, a hardware-constrained RCM.

Referring to FIGS. 10-13, it can be seen that first link 810 has a proximal end 810*a* and a distal end 810*b*. First link 810's straight longitudinal axis 821 extends through and is defined by its proximal and distal ends. It can further be seen that second link 820 has a proximal end 820*a* and a distal end 820*b*. Second link 820 also has an actuator housing portion 820*c* that extends proximally beyond proximal end 820*a* to a proximal actuator housing portion end 820*d*.

Still referring to FIGS. 10-13, the distal end 810*b* of first link 810 is rotatably coupled to the proximal end 820*a* of second link 820 at a revolute joint 815. The axis of rotation of revolute joint 815 defines a longitudinal axis of second link 820. The longitudinal axes of the first and second links are coincident, and these coincident axes are illustrated by axis 821 as shown. Accordingly, the second link 820 can rotate in relation to the first link 810 about an axis that is defined by the rotary joint 815, which may be considered a yaw joint (the term "yaw" is arbitrary and does not indicate a unique coordinate system). It can be seen that as second link 820 rotates in relation to first link 810, second link 820's housing portion 820*c* and its distal end 820*d* orbit around first link 810. It can further be seen that an axis through housing portion proximal end 820*d* and second link distal end 820*b* sweeps along a section of a conical surface having an axis coincident with the longitudinal axis of second link 820.

The second link 820 is rotatably coupled to the third link 830 at a revolute pivot joint 825, which may be considered a pitch joint (the term "pitch" is arbitrary and does not indicate a unique coordinate system). Accordingly, the third link 830 can pivot in relation to the second link 820 about an axis that is defined by the revolute pivot joint 825. At any combination of relative orientation between the links 810, 820, and 830 and motions of the links 810, 820, and 830, the RCM 902 remains fixed in space because of the manipulator device assembly 800 is designed with a hardware-constrained RCM.

Figure 12:
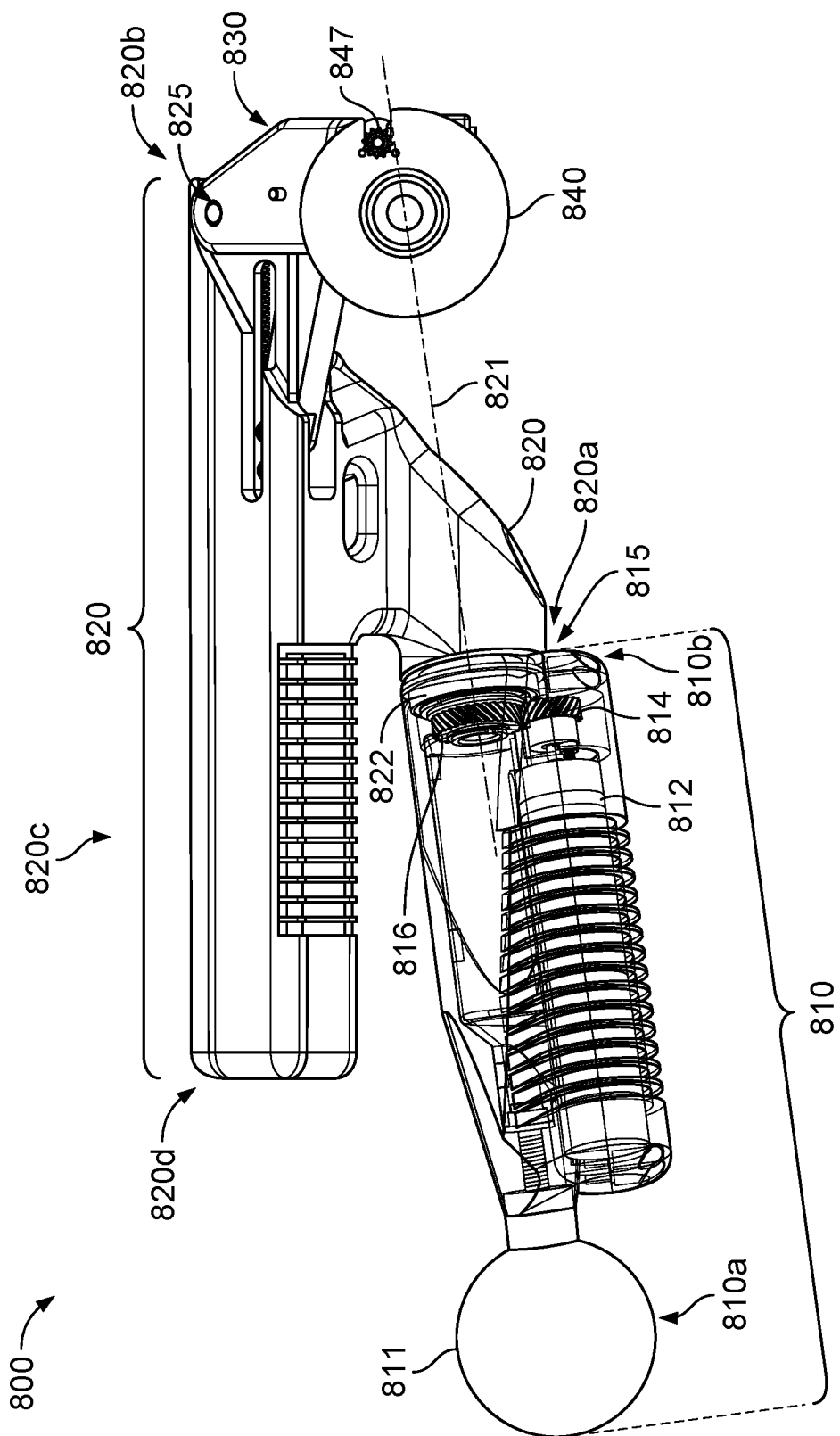
FIG. 12 is a top view of the computer-assisted tele-operated surgery manipulator device of FIG. 10. The first link of the manipulator device is shown transparently.
Figure 13:
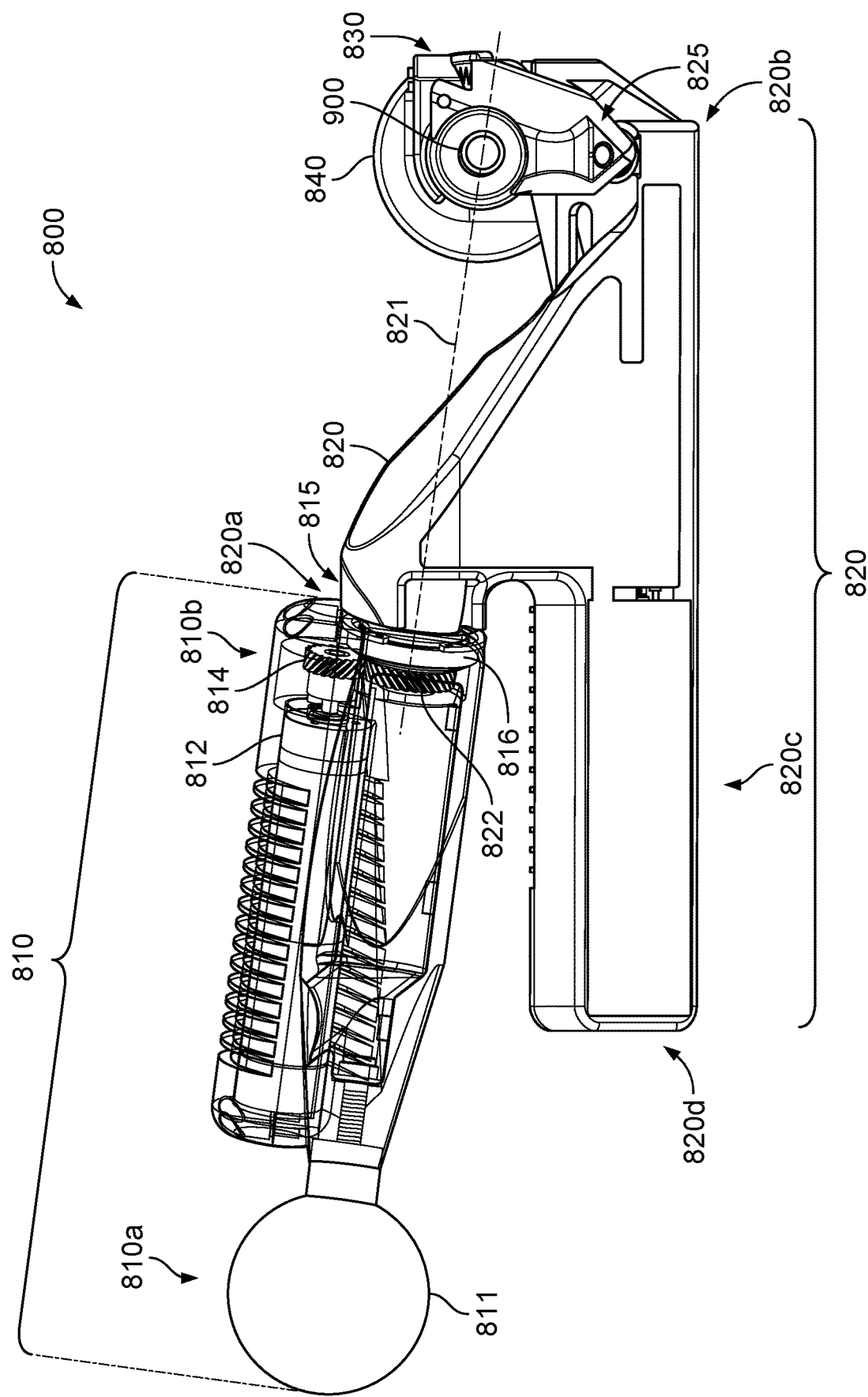
FIG. 13 is a bottom view of the computer-assisted tele-operated surgery manipulator device of FIG. 10 with the first link shown transparently.

Referring to FIGS. 12 and 13, here the first link 810 is shown transparently so that the mechanisms by which the second link 820 is rotatable in relation to the first link 810 can be visualized. In the depicted embodiment, a motor 812 is included in the first link 810. A drive gear 814 is fixed to the drive shaft of the motor 812. Rotation of the motor 812 therefore rotates the drive gear 814. As shown, motor 812 extends proximally from drive gear 814 (i.e., proximally from joint 815).

The drive gear 814 is meshed with a driven gear 822. The driven gear 822 is fixed to the second link 820. Therefore, rotary motion of the driven gear 822 result in corresponding rotary motion of the second link 820. Motor 812 and drive gear 814 are illustrative of various yaw drive assemblies that may be used. As shown, with reference to first link 820's longitudinal axis 821, motor 812's axis of rotation is nonparallel, non-intersecting, and at a shallow acute angle. In other implementations motor 812's axis of rotation may, for example, parallel to or coincident with longitudinal axis 821.

Because the first link 810 is constrained in relation to a set-up structure (e.g., set-up structure 172, FIG. 8), rotation of the drive gear 814 causes the driven gear 822 to rotate around its axis 821. Because the driven gear 822 is fixed to the second link 820, rotation of the driven gear around the axis 821 causes the entire second link 820 to rotate about the axis 821.

The first link 810 also includes a bearing 816. The outer race of the bearing 816 is captured in a stationary relationship to the housing of the first link 810. The inner race of the bearing 816 is coupled with a stub shaft (projecting from the second link 820) that the driven gear 822 is also coupled to. Therefore, the entire second link 820 rotates in relation to the first link 810 about the axis 821 as the motor 812 is actuated. In the depicted embodiment, the axis 821 is defined by the bearing 816 and is coaxial with the driven gear 822. The axis 821 projects through the RCM 902 (FIGS. 10 and 11) and functions as an instrument yaw axis of the manipulator assembly.

Figure 14:
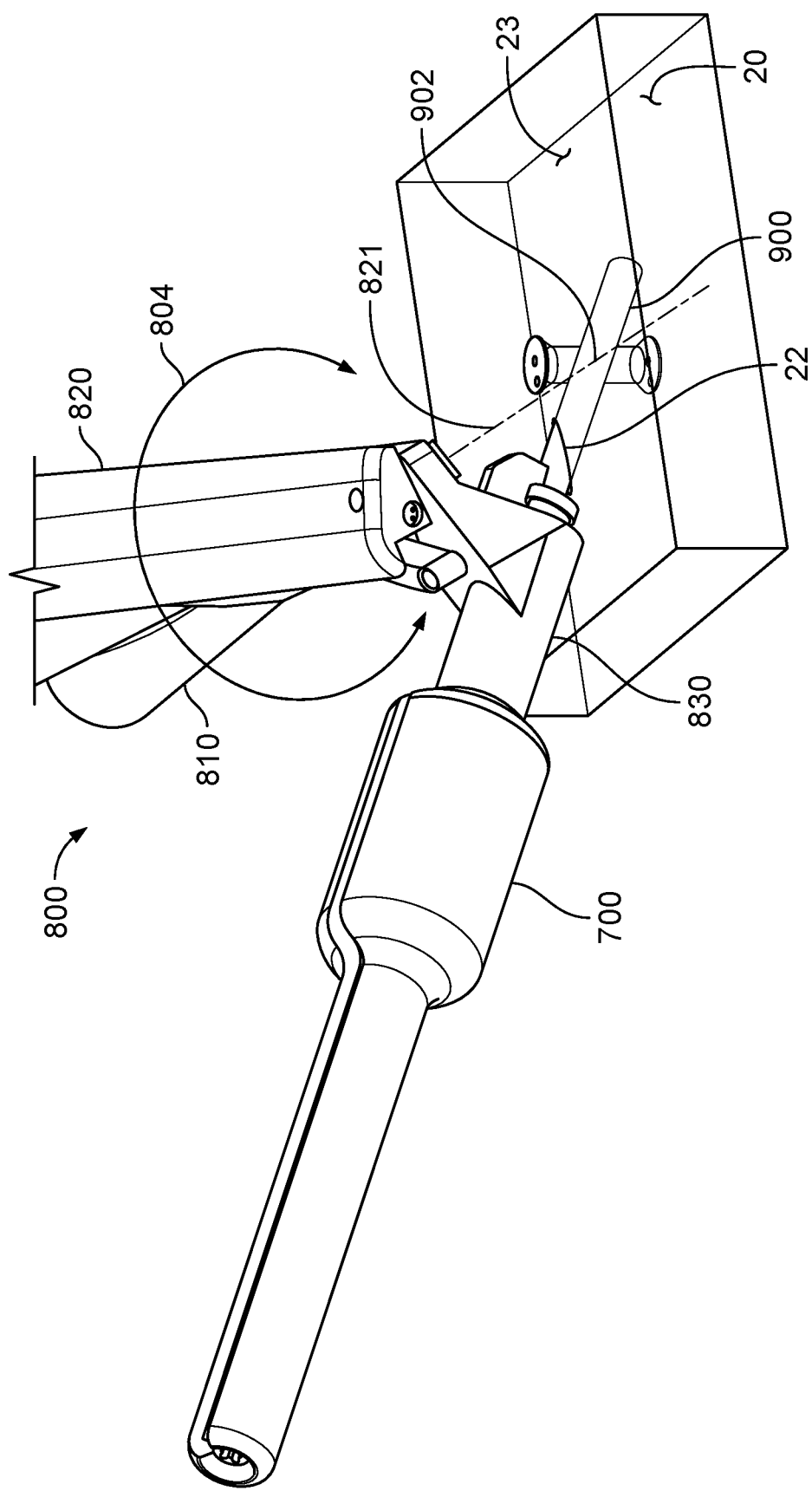
FIG. 14 is a perspective view of the computer-assisted tele-operated surgery manipulator device of FIG. 10 in a first orientation in relation to a body wall.
Figure 15:
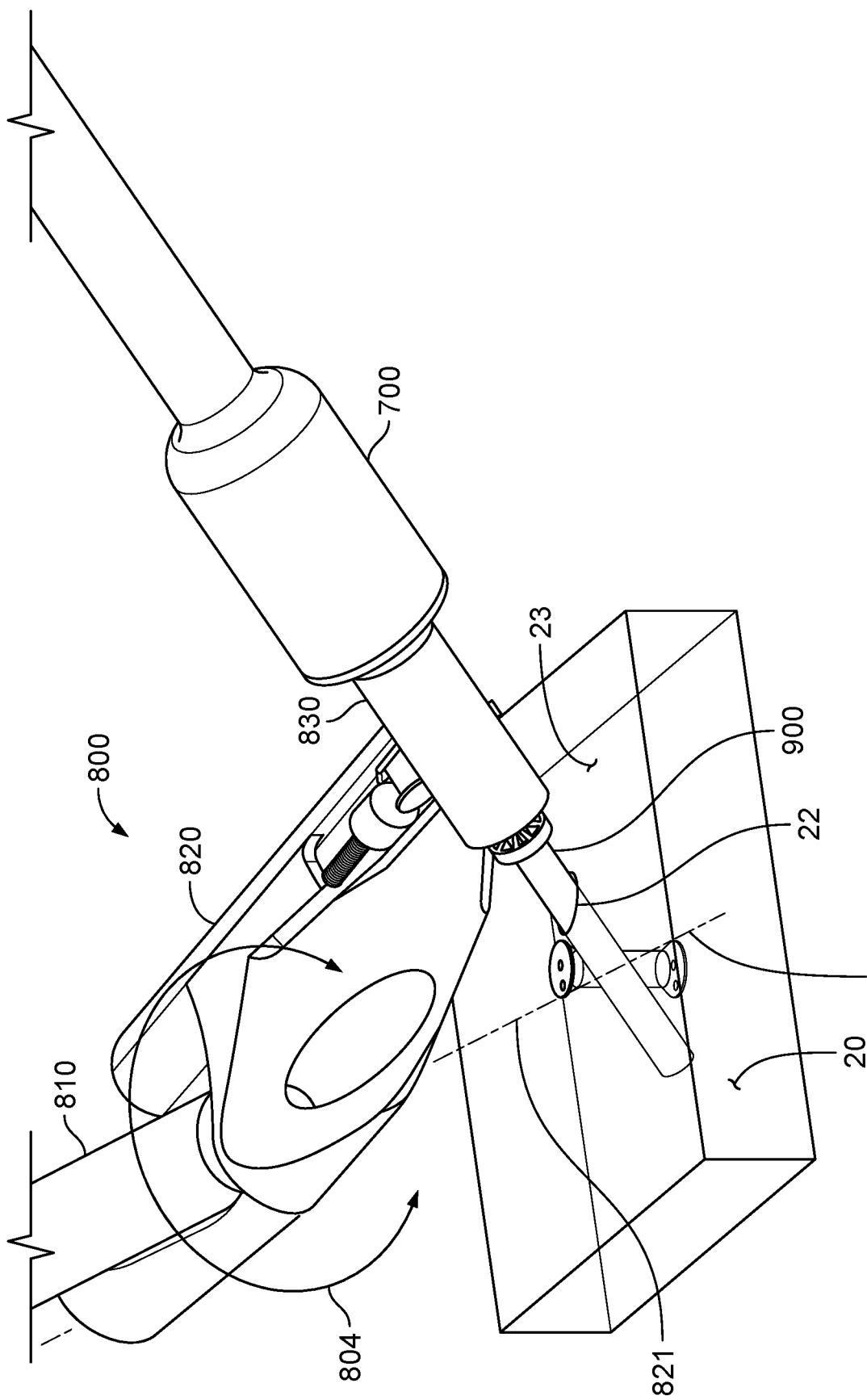
FIG. 15 is a perspective view of the computer-assisted tele-operated surgery manipulator device of FIG. 10 in a second orientation in relation to the body wall.

Referring also to FIGS. 14 and 15, here the manipulator device assembly 800 is shown in relation to a simulated portion of a patient's body wall 20. The difference between FIG. 14 and FIG. 15 is the rotational orientation of the second link 820 in relation to the first link 810. As described above, the second link 820 is rotatable in relation to the first link 810 about the axis 821 as depicted by arrow 804. In some cases, the axis 821 may also be referred to as the yaw axis 821, and rotations of the second link 820 in relation to the first link 810 may be referred to as yaw motions, or simply "yaw." The yaw axis 821 projects through the RCM 902.

One advantageous feature of the manipulator device assembly 800 is that it is designed to facilitate a wide range of yaw motion without contacting the patient's body (e.g., without contacting a surface 23, which may be a skin surface, for example, or without intersecting a plane that includes the RCM 902 and that is perpendicular to the instrument insertion axis 702). In general, yaw range of motion is limited by second link 820's proximity to surface 23 at one extreme (see e.g., FIG. 15) and third link 830's proximity to surface 23 at the other extreme (see e.g., FIG. 14). For example, in some embodiments the second link 820 can be rotated in relation to the first link 810 through an arc (as depicted by arrow 804) that is in a range of about 90° to about 110° (100°±10°), or about 100° to about 120° (110°±10°), or about 110° to about 130° (120°±10°), or about 120° to about 140° (130°±10°), or about 130° to about 150° (140°±10°), or about 110° to about 120° (115°±5°), or about 115° to about 125° (120°±5°), or about 120° to about 130° (125°±5°) without contacting the patient's body and/or without intersecting the plane that includes the RCM 902. It should also be understood that these ranges of rotational motion of the second link 820 in relation to the first link 810 can be realized throughout all possible rotational orientations of the third link 830 in relation to the second link 820 when pivoted at pivot joint 825.

Another advantageous feature of the manipulator device assembly 800 is its operative usability for computer-assisted teleoperated surgery while positioned at a low angle in relation to the surface 23. Such low-angle positioning can provide advantages such as enhanced patient access by the surgical team, greater visualization of the patient, and facilitated communications between the surgical team members because they can more easily see each other. For example, in some embodiments the manipulator device assembly 800 can be oriented such that the angle between the yaw axis 821 and the surface 23 (or, for example, between the yaw axis 821 and a plane that includes the RCM 902) is in a range between about 10° to about 30° (20°±10°), or about 20° to about 40° (30°±10°), or about 30° to about 50° (40°±10°), or about 15° to about 25° (20°±5°), or about 20° to about 30° (25°±5°), or about 25° to about 35° (30°±5°), or about 30° to about 40° (35°±5°). Moreover, the manipulator device assembly 800 can be oriented at these low angles while also allowing for the second link 820 to be rotated in relation to the first link 810 through the arc ranges described above without intersecting the patient's body (or intersecting the plane that includes the RCM 902).

Figure 16:
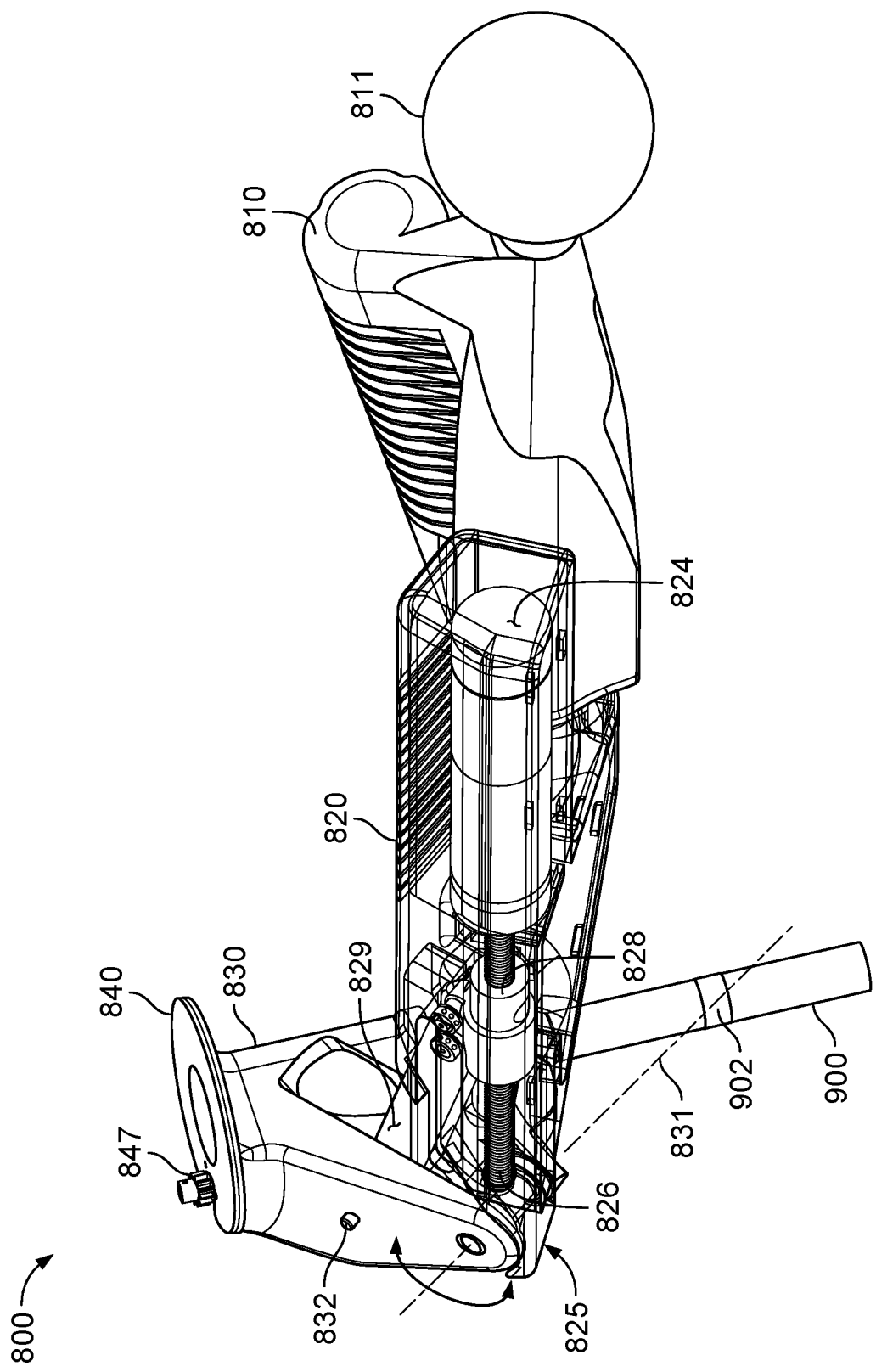
FIG. 16 is another perspective view of the computer-assisted tele-operated surgery manipulator device of FIG. 10. The second link of the manipulator device is shown transparently.
Figure 17:
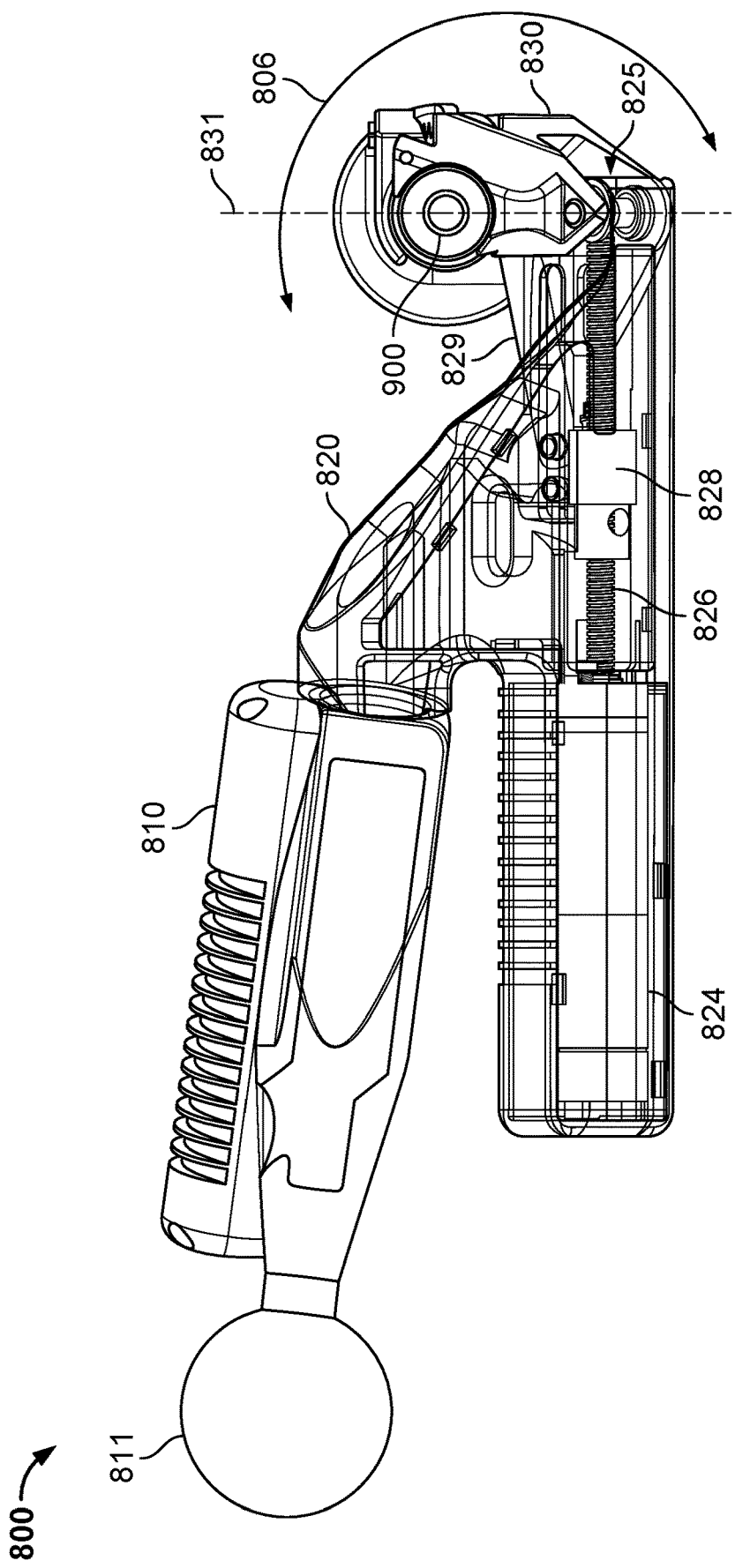
FIG. 17 is another perspective view of the computer-assisted tele-operated surgery manipulator device of FIG. 10 with the second link shown transparently.

Referring to FIGS. 16 and 17, the second link 820 is shown transparently so that the mechanisms by which the third link 830 is rotatable in relation to the second link 820 can be visualized. In the depicted embodiment, a motor 824 is included in the second link 820. A lead screw 826 is coupled to the drive shaft of the motor 824. Rotation of the motor 824 therefore rotates the lead screw 826.

A nut 828 is threadably coupled to the lead screw 826. The nut 828 is constrained from rotating in relation to the housing of the second link 820. Therefore, as the motor 824 drives rotation of the lead screw 826, the nut 828 is caused to translate along the longitudinal axis of the lead screw 826.

A pitch drive link 829 has a first end that is pivotably coupled to the nut 828 and a second end that is pivotably coupled to the third link 830 at a pivot joint 832. The pivot joint 832 is spaced apart from the pivot joint 825. Therefore, as the motor 824 drives rotation of the lead screw 826, the nut 828 is caused to translate along the longitudinal axis of the lead screw 826, and the link 829 causes the third link 830 to pivot about the pivot joint 825 in relation to the second link 820. The pivoting motion of the third link 830 in relation to the second link 820 is depicted by arrow 806. The entire third link 830 pivots in relation to second link 820 about the axis 831 as the motor 824 is actuated. In the depicted embodiment, the axis 831 is defined by the pivot joint 825 (which acts as a hinge between the second link 820 and the third link 830). The axis 831 projects through the RCM 902 and functions as an instrument pitch axis of the manipulator assembly.

The motor 824, lead screw 826, and nut 828 are illustrative of various linear actuators that may be used, including ball screw, chain, belt, hydraulic, pneumatic, electromagnetic, and the like. Such linear actuators and the pitch drive link 829 are illustrative of various pitch drive assemblies that may be used to rotate third link 830 around pitch axis 831.

It should be understood that in the context of manipulator device assembly 800, the rotational motion between the first link 810 and the second link 820 is a different type of motion than the rotational motion between the second link 820 and the third link 830. The third link 830 pivots in relation to the second link 820 because the links are conjoined at the pivot joint 825 (which acts like a hinge), and so third link 830 generally orbits around axis 831. The second link 820 rotates in relation to the first link 810 because the links are conjoined at the rotary joint 815 which allows the second link 820 to rotate in relation to the first link 810 generally in-line around axis 821.

Figure 18:
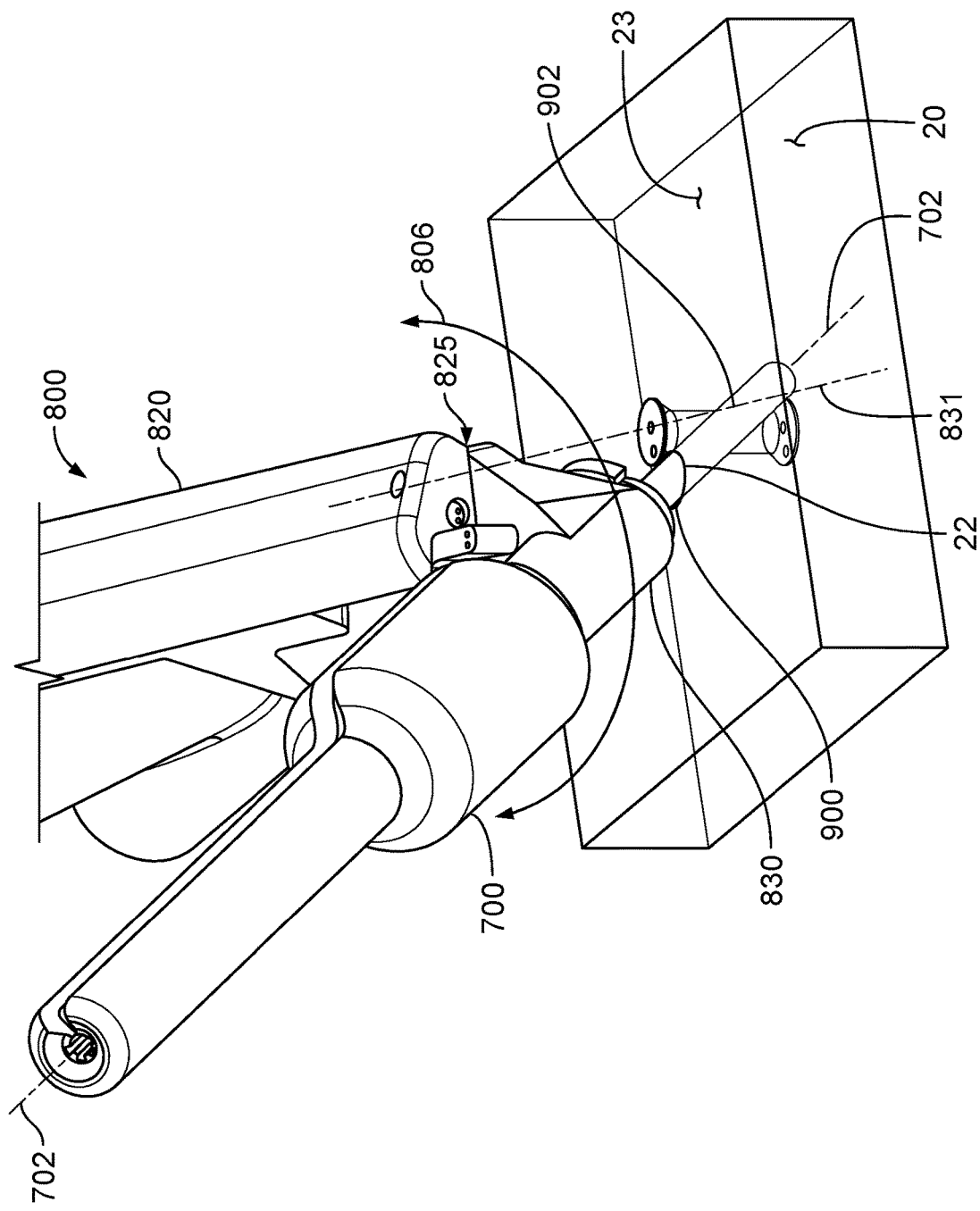
FIG. 18 is a perspective view of the computer-assisted tele-operated surgery manipulator device of FIG. 10 in a third orientation in relation to the body wall.
Figure 19:
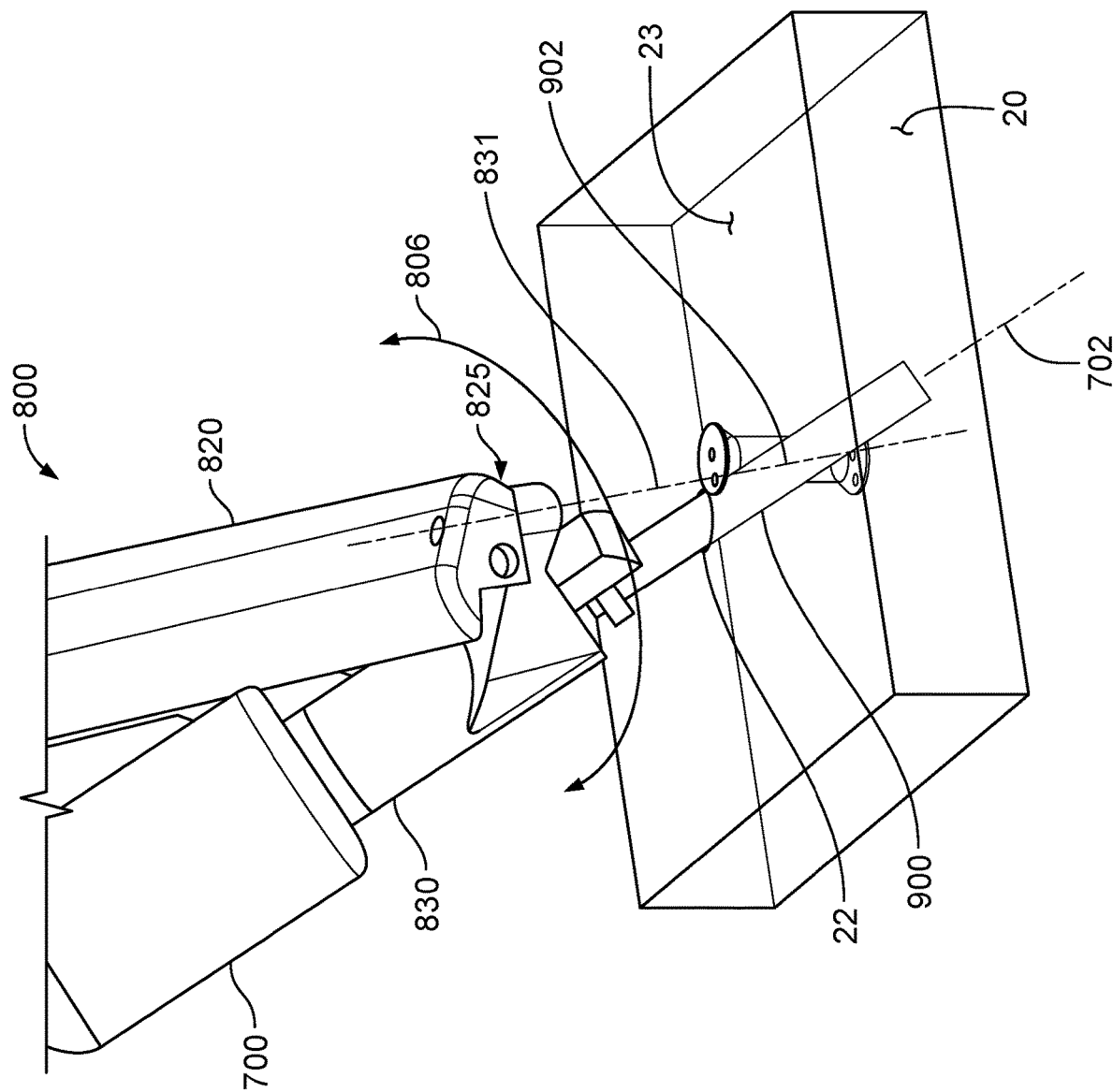
FIG. 19 is a perspective view of the computer-assisted tele-operated surgery manipulator device of FIG. 10 in a fourth orientation in relation to the body wall.

Referring also to FIGS. 18 and 19, the manipulator device assembly 800 is shown in relation to a simulated portion of a patient's body wall 20. The difference between FIG. 18 and FIG. 19 is the rotational orientation of the third link 830 in relation to the second link 820. As described above, the third link 830 is pivotable in relation to the second link 820 about the axis 831, as depicted by arrow 806. In some cases, the axis 831 may also be referred to as the pitch axis 831, and pivotal motions of the third link 830 in relation to the second link 820 may be referred to as pitch motions, or simply "pitch." The pitch axis 831 projects through the RCM 902.

In the depicted embodiment, the pitch axis 831 is non-orthogonal to the insertion axis 702. The pitch axis 831 remains non-orthogonal to the insertion axis 702 throughout all rotational orientations of the second link 820 around yaw axis 821 in relation to the first link 810, throughout all rotational orientations of the third link 830 around pitch axis 831 in relation to the second link 820, and throughout all combinations thereof. In some embodiments, the angle between the pitch axis 831 and the insertion axis 702 is in a range between about 10° to about 30°, or about 20° to about 40°, or about 30° to about 50°, or about 15° to about 25°, or about 20° to about 25, or about 25° to about 35°, or about 30° to about 40°, or about 25° to about 30°, or about 30° to about 35°.

It can be seen that as the third link 830 pivots in relation to the second link 820, insertion axis 702 sweeps across a portion of a conical surface having an apex at RCM 902. It can also be seen that at a unique rotational orientation of the third link 830 around the pitch axis 831 with reference to the second link 820, instrument insertion axis 702 will be perpendicular to yaw axis 821. And so at this unique rotational orientation around pitch axis 831, rotation of the second link 820 around yaw axis 821 with reference to the first link 810 sweeps the instrument insertion axis 702 across a circular sector surface having a center at RCM 902. It can also be seen that at rotational orientations of the third link 830 around the pitch axis 831 with reference to the second link 820 other than this unique rotational orientation around pitch axis 831, rotation of the second link 820 around the yaw axis 821 with reference to the first link 810 sweeps the instrument insertion axis 702 across a portion of a conical surface having an apex at RCM 902. The portions of the conical surfaces across which instrument insertion axis 702 is swept by rotation around the yaw axis 821 and rotation around the pitch axis 831 are different from each other.

Thus it can be seen that RCM 902 is constrained by manipulator device assembly 800's hardware, and it is defined by the intersection of insertion axis 702, yaw axis 821, and pitch axis 831. As the surgeon commands the instrument end effector 650 to move in various directions at the surgical site by moving a master input device 42, the controller illustrated by processor 43 correspondingly controls rotation of the instrument as a whole along axis 702, around axis 821, and around axis 831 to place the end effector at the desired position in space at the surgical site. Similarly, the controller controls orientation of end effector 650 by controlling rotation around axis 702, and by moving the end effector in pitch and yaw with reference to instrument shaft 640. Manipulator device assembly 800 provides a compact, low profile, large range of motion teleoperated manipulator for use during telesurgery.

In some embodiments, the manipulator device assembly 800 may include electronic sensors and the like for various advantageous purposes. For example, encoders may be coupled to the drive trains of the motorized pitch, roll, and/or yaw drive (adjustment) mechanisms. In some embodiments, position sensors may be used that can positively identify the locations of the movable components of the manipulator device 800.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

We claim:

1. A teleoperated surgical system comprising:
   an elongate first link comprising a proximal end, a distal end, and a longitudinal axis defined between the proximal and distal ends of the first link;
   a second link rotatably coupled to the first link at a revolute yaw joint having an axis of rotation that defines an instrument yaw axis coincident with the longitudinal axis of the first link;
   a third link rotatably coupled to the second link at a revolute pitch joint having an axis of rotation that defines an instrument pitch axis;
   a surgical instrument actuator comprising a proximal end, a distal end, and an instrument insertion axis defined between the proximal and distal ends of the instrument actuator, wherein the surgical instrument actuator is coupled to the third link at the distal end of the surgical instrument actuator;
   wherein the yaw axis, the pitch axis, and the instrument insertion axis are retained in movable orientations to each other and consistently intersect at a remote center of motion; and
   wherein rotation of the third link around the pitch axis with reference to the second link sweeps the instrument insertion axis to trace a portion of a first conical shape having an apex at the remote center of motion.

2. The teleoperated surgical system of claim 1, wherein:
   at a particular first rotational orientation of the third link around the pitch axis with reference to the second link, rotation of the second link around the yaw axis with reference to the first link sweeps the instrument insertion axis across a circular sector surface having a center at the remote center of motion; and
   at rotational orientations of the third link around the pitch axis with reference to the second link other than the first rotational orientation, rotation of the second link around the yaw axis with reference to the first link sweeps the instrument insertion axis to trace a second conical shape having an apex at the remote center of motion.

3. The teleoperated surgical system of claim 1, further comprising:
a revolute roll joint;
wherein the surgical instrument actuator is coupled to the third link via the roll joint, the roll joint defines an axis of rotation coincident with the instrument insertion axis, and the surgical instrument actuator rotates at the roll joint with reference to the third link around the instrument insertion axis.

4. The teleoperated surgical system of claim 3, wherein:
at a particular first rotational orientation of the third link around the pitch axis with reference to the second link, rotation of the second link around the yaw axis with reference to the first link sweeps the instrument insertion axis across a circular sector surface having a center at the remote center of motion; and
at rotational orientations of the third link around the pitch axis with reference to the second link other than the first rotational orientation, rotation of the second link around the yaw axis with reference to the first link sweeps the instrument insertion axis to trace a second conical shape having an apex at the remote center of motion.

5. The teleoperated surgical system of claim 1, wherein:
the second link comprises a pitch drive assembly;
the pitch drive assembly comprises a linear actuator and a pitch drive link coupled to the linear actuator; and
the pitch drive assembly is coupled between the second link and the third link and drives rotation of the third link around the pitch axis.

6. The teleoperated surgical system of claim 1, further comprising:
a yaw drive assembly coupled to the second link;
wherein the yaw drive assembly is engaged with the first link and drives rotation of the second link around the yaw axis.

7. The teleoperated surgical system of claim 1, further comprising:
a roll drive assembly coupled to the third link;
wherein the roll drive assembly is engaged with the surgical instrument actuator and drives rotation of the surgical instrument actuator around the instrument insertion axis.

8. The teleoperated surgical system of claim 1, wherein:
the teleoperated surgical system is configured to insert a surgical instrument along the surgical instrument insertion axis.

9. The teleoperated surgical system of claim 1, wherein:
the teleoperated surgical system is configured to have a range of motion around the yaw axis of at least 100° during surgery.

10. The teleoperated surgical system of claim 1, wherein:
the teleoperated surgical system is configured to have a range of motion around the yaw axis of at least 120° during surgery.

11. The teleoperated surgical system of claim 1, wherein:
the teleoperated surgical system is configured to have a range of motion around the yaw axis of at least 140° during surgery.

12. The teleoperated surgical system of claim 1, wherein:
the teleoperated surgical system is configured to operate during surgery with the yaw axis at 30° with reference to a plane defined by the remote center of motion and a plane perpendicular to the instrument insertion axis.

13. The teleoperated surgical system of claim 1, wherein:
the teleoperated surgical system is configured to operate during surgery with the yaw axis at 20° with reference to a plane defined by the remote center of motion and a plane perpendicular to the instrument insertion axis.

14. The teleoperated surgical system of claim 1, wherein:
the teleoperated surgical system is configured to operate during surgery with the yaw axis at 10° with reference to a plane defined by the remote center of motion and a plane perpendicular to the instrument insertion axis.

15. The teleoperated surgical system of claim 1, wherein:
the proximal end of the first link is configured to couple with a non-teleoperated setup structure.

16. The teleoperated surgical system of claim 1, wherein:
the third link is configured to removably couple with an instrument cannula aligned with the insertion axis.

17. The teleoperated surgical system of claim 1, wherein:
the surgical instrument actuator is releasably coupled to and is readily detachable from the third link such that the surgical instrument actuator can be interchanged with a second surgical instrument actuator.

18. The teleoperated surgical system of claim 1, further comprising:
a setup structure having a proximal end and a distal end;
wherein the distal end of the setup structure is directly coupled to the proximal end of the first link; and
wherein the proximal end of the setup structure is directly coupled to a mechanical ground.

19. The teleoperated surgical system of claim 18, wherein:
the mechanical ground comprises an operating room table.

20. The teleoperated surgical system of claim 1, further comprising:
a user control unit comprising a user input device and a controller;
wherein the first link, the second link, the third link, and the surgical instrument actuator together comprise a teleoperated surgical manipulator; and
wherein user inputs at the user input device teleoperate the manipulator via the controller to move a surgical instrument with reference to the yaw axis, the pitch axis, and the instrument insertion axis.

* * * * *